United States Patent
MacFarland et al.

(10) Patent No.: US 7,780,652 B2
(45) Date of Patent: Aug. 24, 2010

(54) SYSTEM AND METHOD FOR FLEXIBLE ARCHITECTURE FOR DERMATOLOGIC TREATMENTS UTILIZING MULTIPLE LIGHT SOURCES

(75) Inventors: Dean A. MacFarland, Magnolia, MA (US); Richard Canant, Pacifica, CA (US); David A. Gollnick, San Francisco, CA (US); Greg Spooner, Kensington, CA (US); Kevin P. Connors, San Francisco, CA (US)

(73) Assignee: Cutera, Inc., Brisbane, CA (US)

( * ) Notice: Subject to any disclaimer, the term of this patent is extended or adjusted under 35 U.S.C. 154(b) by 103 days.

(21) Appl. No.: 12/001,157

(22) Filed: Dec. 10, 2007

(65) Prior Publication Data

US 2008/0097419 A1    Apr. 24, 2008

Related U.S. Application Data

(63) Continuation of application No. 10/788,821, filed on Feb. 27, 2004, now Pat. No. 7,326,199.

(60) Provisional application No. 60/540,981, filed on Jan. 30, 2004, provisional application No. 60/532,016, filed on Dec. 22, 2003.

(51) Int. Cl.
*A61B 18/20* (2006.01)
(52) U.S. Cl. .................. 606/1; 606/9; 606/10; 607/88; 607/89
(58) Field of Classification Search ............ 606/1, 606/3–23; 607/88–95; 600/101–105, 108; 128/898
See application file for complete search history.

(56) References Cited

U.S. PATENT DOCUMENTS

| 634,113 | A | 3/1950 | Riley |
| 2,699,771 | A | 1/1955 | Rüttger-Pelli .............. 128/24.1 |

(Continued)

FOREIGN PATENT DOCUMENTS

| CA | 968854 | 6/1975 | .................... 326/4 |

(Continued)

OTHER PUBLICATIONS

R.M. Adrian, "Treatment of Facial Telangiectasia Using the VersaPulse® Variable Pulse Width Frequency Doubled Neodymium:YAG Laser: A Case Report," 2 pages in length.

(Continued)

*Primary Examiner*—Ahmed M Farah
(74) *Attorney, Agent, or Firm*—Morrison & Foerster LLP

(57) ABSTRACT

A system and method for providing light treatments to a patients skin, which could include both dermal and epidermal regions. The system and method utilize multiple hand pieces where each hand piece can deliver light from a different light source. The system and method provide for control over the different light source corresponding to the different hand pieces based on whether the hand pieces are held in storage positions in a hand piece management unit. A control unit of the system provides operates to cause a user interface display to communicate information to a user based on the positions of the different hand pieces. Further, the system and method can provide a user with access to different aspects of the systems operation based on the positions of the hand pieces.

14 Claims, 13 Drawing Sheets

U.S. PATENT DOCUMENTS

| | | | |
|---|---|---|---|
| 3,327,712 A | 6/1967 | Kaufman et al. | 128/398 |
| 3,538,919 A | 11/1970 | Meyer | 606/36 |
| 3,648,706 A | 3/1972 | Holzer | 128/395 |
| 3,693,623 A | 9/1972 | Harte et al. | 128/303.1 |
| 3,834,391 A | 9/1974 | Block | 606/9 |
| 3,867,948 A | 2/1975 | Kallenborn | 128/395 |
| 3,900,034 A | 8/1975 | Katz et al. | 607/89 |
| 3,986,262 A * | 10/1976 | Casillas | 433/28 |
| 4,020,383 A | 4/1977 | Labadini et al. | 313/344 |
| 4,022,534 A | 5/1977 | Kishner | 356/210 |
| 4,106,198 A * | 8/1978 | Childress | 433/28 |
| 4,122,853 A | 10/1978 | Smith | 606/4 |
| 4,233,493 A | 11/1980 | Nath | 219/354 |
| 4,298,005 A | 11/1981 | Mutzhas | 128/396 |
| 4,388,924 A | 6/1983 | Weissman et al. | 606/9 |
| 4,461,294 A | 7/1984 | Baron | 606/5 |
| 4,505,545 A | 3/1985 | Salia-Munoz | 350/321 |
| 4,539,987 A | 9/1985 | Nath et al. | 128/303.1 |
| 4,608,978 A | 9/1986 | Rohr | 128/303.1 |
| 4,608,990 A | 9/1986 | Elings | 128/633 |
| 4,617,926 A | 10/1986 | Sutton | 606/9 |
| 4,658,823 A | 4/1987 | Beddoe et al. | 128/396 |
| 4,667,658 A | 5/1987 | Guibert | 128/24.1 |
| 4,686,986 A | 8/1987 | Fenyö et al. | 128/396 |
| 4,733,660 A | 3/1988 | Itzkan | 606/9 |
| 4,747,660 A | 5/1988 | Nishioka et al. | 350/96.25 |
| 4,757,431 A | 7/1988 | Cross et al. | 362/261 |
| 4,784,135 A | 11/1988 | Blum et al. | 128/303.1 |
| 4,813,412 A | 3/1989 | Yamazaki et al. | 128/303.13 |
| 4,819,669 A | 4/1989 | Politzer | 132/200 |
| 4,829,262 A | 5/1989 | Furumoto | 330/4.3 |
| 4,860,172 A | 8/1989 | Schlager et al. | 362/32 |
| 4,884,568 A | 12/1989 | Hahn | 128/303.1 |
| 4,917,084 A | 4/1990 | Sinofsky | 606/7 |
| 4,930,504 A | 6/1990 | Diamantopoulos et al. | 128/395 |
| 4,950,880 A | 8/1990 | Hayner | 250/201.9 |
| 4,976,709 A | 12/1990 | Sand | 606/5 |
| 5,000,752 A | 3/1991 | Hoskin et al. | 606/9 |
| 5,057,104 A | 10/1991 | Chess | 606/9 |
| 5,059,192 A | 10/1991 | Zaias | 606/9 |
| 5,139,494 A | 8/1992 | Freiberg | 606/3 |
| 5,161,526 A | 11/1992 | Hellwing et al. | 128/395 |
| 5,182,857 A | 2/1993 | Simon | 30/34.05 |
| 5,207,671 A | 5/1993 | Franken et al. | 606/9 |
| 5,217,455 A | 6/1993 | Tan | 606/9 |
| 5,226,907 A | 7/1993 | Tankovich | 606/133 |
| 5,258,989 A | 11/1993 | Raven | 372/6 |
| 5,259,380 A | 11/1993 | Mendes et al. | 607/115 |
| 5,282,797 A | 2/1994 | Chess | 606/9 |
| 5,290,273 A | 3/1994 | Tan | 606/9 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,320,618 A | 6/1994 | Gustafsson | 606/9 |
| 5,336,217 A | 8/1994 | Buys et al. | 606/9 |
| 5,337,741 A | 8/1994 | Diamond | 600/8 |
| 5,344,418 A | 9/1994 | Ghaffari | 606/9 |
| 5,344,434 A | 9/1994 | Talmore | 607/88 |
| 5,374,265 A | 12/1994 | Sand | 606/5 |
| 5,397,327 A | 3/1995 | Koop et al. | 606/17 |
| 5,405,368 A | 4/1995 | Eckhouse | 607/88 |
| 5,409,479 A | 4/1995 | Dew et al. | 606/9 |
| 5,425,728 A | 6/1995 | Tankovich | 606/9 |
| 5,441,531 A | 8/1995 | Zarate et al. | 607/90 |
| 5,458,596 A | 10/1995 | Lax et al. | 606/31 |
| 5,474,549 A | 12/1995 | Ortiz et al. | 606/9 |
| 5,486,172 A | 1/1996 | Chess | 606/20 |
| 5,511,563 A | 4/1996 | Diamond | 128/848 |
| 5,522,813 A | 6/1996 | Trelles | 606/2 |
| 5,527,350 A | 6/1996 | Grove et al. | 607/89 |
| 5,569,979 A | 10/1996 | Scott et al. | 313/636 |
| 5,572,091 A | 11/1996 | Langer et al. | 313/636 |
| 5,591,157 A | 1/1997 | Hennings et al. | 606/3 |
| 5,595,568 A | 1/1997 | Anderson et al. | 606/9 |
| 5,611,795 A | 3/1997 | Slatkine et al. | 606/9 |
| 5,620,478 A | 4/1997 | Eckhouse | 607/88 |
| 5,660,836 A | 8/1997 | Knowlton | 424/400 |
| 5,683,380 A | 11/1997 | Eckhouse et al. | 606/9 |
| 5,688,235 A * | 11/1997 | Sakurai et al. | 604/22 |
| 5,735,844 A | 4/1998 | Anderson et al. | 606/9 |
| 5,755,753 A | 5/1998 | Knowlton | 607/98 |
| 5,769,844 A | 6/1998 | Ghaffari | 606/16 |
| 5,769,878 A | 6/1998 | Kamei | 607/88 |
| 5,782,895 A | 7/1998 | Zarate et al. | 607/88 |
| 5,807,261 A | 9/1998 | Benaron et al. | 600/473 |
| 5,810,801 A | 9/1998 | Anderson et al. | 606/9 |
| 5,814,040 A | 9/1998 | Nelson et al. | 606/9 |
| 5,820,625 A | 10/1998 | Izawa et al. | 606/9 |
| 5,830,208 A | 11/1998 | Muller | 606/9 |
| 5,843,074 A * | 12/1998 | Cocilovo | 606/10 |
| 5,843,143 A | 12/1998 | Whitehurst | 607/88 |
| 5,885,274 A | 3/1999 | Fullmer et al. | 606/9 |
| 5,919,219 A | 7/1999 | Knowlton | 607/102 |
| 5,964,749 A | 10/1999 | Eckhouse et al. | 606/9 |
| 5,989,283 A | 11/1999 | Wilkens | 607/88 |
| 6,015,404 A | 1/2000 | Altshuler et al. | 606/9 |
| 6,050,990 A | 4/2000 | Tankovich et al. | 606/9 |
| 6,080,146 A | 6/2000 | Altshuler et al. | 606/9 |
| 6,080,147 A | 6/2000 | Tobinick | 606/9 |
| 6,096,066 A | 8/2000 | Chen et al. | 607/88 |
| 6,120,497 A | 9/2000 | Anderson et al. | 606/9 |
| 6,168,590 B1 | 1/2001 | Neev | 606/9 |
| 6,171,332 B1 | 1/2001 | Whitehurst | 607/89 |
| 6,228,074 B1 | 5/2001 | Almeida | 606/9 |
| 6,235,015 B1 | 5/2001 | Mead, III et al. | 606/9 |
| 6,241,753 B1 | 6/2001 | Knowlton | 607/99 |
| 6,273,884 B1 | 8/2001 | Altshuler et al. | 606/9 |
| 6,280,438 B1 | 8/2001 | Eckhouse et al. | 606/9 |
| 6,319,273 B1 | 11/2001 | Chen et al. | 607/88 |
| 6,377,855 B1 | 4/2002 | Knowlton | 607/101 |
| 6,381,498 B1 | 4/2002 | Knowlton | 607/101 |
| 6,383,176 B1 | 5/2002 | Connors et al. | 606/9 |
| 6,387,089 B1 | 5/2002 | Kreindel et al. | 606/9 |
| 6,405,090 B1 | 6/2002 | Knowlton | 607/102 |
| 6,413,253 B1 | 7/2002 | Koop et al. | 606/27 |
| 6,443,978 B1 | 9/2002 | Zharov | 607/91 |
| 6,453,202 B1 | 9/2002 | Knowlton | 607/102 |
| 6,461,866 B1 | 10/2002 | Whitehurst | 435/325 |
| 6,482,199 B1 | 11/2002 | Neev | |
| 6,485,484 B1 | 11/2002 | Connors et al. | 606/9 |
| 6,508,813 B1 | 1/2003 | Altshuler | 606/9 |
| 6,511,475 B1 | 1/2003 | Altshuler et al. | 606/9 |
| 6,517,532 B1 | 2/2003 | Altshuler et al. | 606/9 |
| 6,524,329 B1 | 2/2003 | Benedict | 607/88 |
| 6,558,372 B1 | 5/2003 | Altshuler | 606/2 |
| 6,569,155 B1 | 5/2003 | Connors et al. | 606/9 |
| 6,592,611 B1 | 7/2003 | Zawada | 607/89 |
| 6,602,275 B1 | 8/2003 | Sullivan | 607/88 |
| 6,605,080 B1 | 8/2003 | Altshuler et al. | 606/3 |
| 6,623,423 B2 * | 9/2003 | Sakurai et al. | 600/104 |
| 6,648,904 B2 | 11/2003 | Altshuler et al. | 607/96 |
| 6,653,618 B2 | 11/2003 | Zenzie | 250/221 |
| 6,663,620 B2 | 12/2003 | Altshuler et al. | 606/9 |
| 6,723,090 B2 | 4/2004 | Altshuler et al. | 606/9 |
| 6,743,222 B2 | 6/2004 | Durkin et al. | 606/9 |
| 6,749,624 B2 | 6/2004 | Knowlton | 607/104 |
| 6,962,583 B2 | 11/2005 | Kadziauskas et al. | 606/6 |
| 6,989,023 B2 * | 1/2006 | Black | 607/90 |
| 7,179,278 B2 * | 2/2007 | Schikora | 607/89 |
| 7,326,199 B2 * | 2/2008 | MacFarland et al. | 606/10 |
| 2002/0055092 A1 | 5/2002 | Hochman | 435/4 |
| 2002/0087179 A1 * | 7/2002 | Culp et al. | 606/167 |
| 2002/0091377 A1 | 7/2002 | Anderson et al. | 606/9 |
| 2002/0128635 A1 | 9/2002 | Altshuler et al. | 606/9 |

| | | | |
|---|---|---|---|
| 2002/0161357 A1 | 10/2002 | Anderson et al. | 606/9 |
| 2002/0173780 A1 | 11/2002 | Altshuler et al. | 606/9 |
| 2002/0198575 A1 | 12/2002 | Sullivan | 607/88 |
| 2003/0004499 A1 | 1/2003 | McDaniel | 606/3 |
| 2003/0023283 A1 | 1/2003 | McDaniel | 607/88 |
| 2003/0032900 A1 | 2/2003 | Ella | 601/6 |
| 2003/0032950 A1 | 2/2003 | Altshuler et al. | 606/9 |
| 2003/0045916 A1 | 3/2003 | Anderson et al. | 607/89 |
| 2003/0055413 A1 | 3/2003 | Altshuler et al. | 606/9 |
| 2003/0055414 A1 | 3/2003 | Altshuler et al. | 606/9 |
| 2003/0057875 A1 | 3/2003 | Inochkin et al. | 351/224 |
| 2003/0065313 A1 | 4/2003 | Koop et al. | 606/9 |
| 2003/0065314 A1 | 4/2003 | Altshuler et al. | 606/9 |
| 2003/0125788 A1 | 7/2003 | Long | 607/133 |
| 2003/0130709 A1 | 7/2003 | Constance Haber et al. | 607/88 |
| 2003/0195494 A1 | 10/2003 | Altshuler et al. | 606/9 |
| 2003/0199859 A1 | 10/2003 | Altshuler et al. | 606/9 |
| 2004/0010298 A1 | 1/2004 | Altshuler et al. | 607/88 |
| 2004/0024388 A1 | 2/2004 | Altshuler | 606/2 |
| 2004/0034319 A1 | 2/2004 | Anderson et al. | 604/20 |
| 2004/0093042 A1 | 5/2004 | Altshuler et al. | 607/88 |
| 2004/0147985 A1 | 7/2004 | MacFarland et al. | 607/90 |
| 2006/0074405 A1* | 4/2006 | Malackowski et al. | 606/1 |

FOREIGN PATENT DOCUMENTS

| | | | |
|---|---|---|---|
| CA | 1041610 | 10/1978 | 326/16 |
| DE | 33 47 730 A1 | 7/1985 | |
| DE | 39 06 860 A1 | 9/1989 | |
| EP | 0 565 331 A2 | 10/1993 | |
| GB | 2 360 946 A | 10/2001 | |
| JP | 4-98795 | 3/1992 | |
| WO | WO 86/02783 | 5/1986 | |
| WO | WO 89/00871 | 2/1989 | |
| WO | WO 95/15725 | 6/1995 | |
| WO | WO 96/22813 | 8/1996 | |
| WO | WO 97/37723 | 10/1997 | |
| WO | WO 98/24514 | 6/1998 | |
| WO | WO 98/38933 | 9/1998 | |
| WO | WO 98/51235 | 11/1998 | |
| WO | WO 99/07438 | 2/1999 | |
| WO | WO 99/11324 | 3/1999 | |
| WO | WO 00/54685 | 9/2000 | |
| WO | WO 00/54685 A3 | 9/2000 | |

OTHER PUBLICATIONS

J.C. Allain et al., "Isometric Tensions Developed During the Hydrothermal Swelling of Rat Skin," *Connective Tissue Research*, vol. 7, pp. 127-133 (1980).

R.R. Anderson, "Clinical Use of the Lightsheer Diode Laser System," (reprinted with permission from Harvard Medical School, Mar. 1998) from the website located at http://www.lasertraining.com/med-8.htm, printed Sep. 15, 1998, 5 pages long.

R.R. Anderson et al., *International Advances in Surgical Oncology* (*Volume 5*), section entitled "Lasers in Dermatology Provide a Model for Exposing New Applications in Surgical Oncology," publisher Alan R. Liss, Inc. (1982), pp. 341-358.

R.R. Anderson, Brochure by Palomar Medical Technologies, Inc., "A Clinical Study on Ruby Lasers for Permanent Hair Reduction," 8 pages in length (1999).

R.R. Anderson, "Safety and Efficacy of the Palomar Ruby Laser for Hair Removal," Harvard Medical School, Mar. 1997, 2 pages in length.

R.R. Anderson, "Hair Removal Using Light," Harvard Medical School, Mar. 1997, 2 pages in length.

R.R. Anderson, "Clinical Use of the EpiLaser® System," 8 pages in length (1998).

G.B. Bartley et al., "An Experimental Study to Compare Methods of Eyelash Ablation," *Ophthalmology*, vol. 94, pp. 1286-1289 (1987).

J.-L. Boulnois, "Photophysical Processes in Recent Medical Laser Developments: a Review," *Lasers in Medical Science*, vol. 1, pp. 47-64 (1986).

Brochure, from Laser Aesthetics, Inc., "The Cool Touch Laser," one page in length.

C. Chess et al., "Cool Laser Optics Treatment of Large Telangiectasia of the Lower Extremities," *J. Dermatol. Surg. Oncol.*, vol. 19, pp. 74-80 (1993).

W.F. Coulson et al., "Nonablative Laser Treatment of Facial Rhytides: Animal Study," *Abstract of BiOS '98 Symposium* [*Cutaneous Applications of Lasers*], Jan. 24-30, 1998 in San Jose, CA, one page in length.

C.C. Danielsen, "Age-related thermal stability and susceptibility to proteolysis of rat bone collagen," *Biochem J.*, vol. 272, No. 3, Dec. 15, 1990, pp. 697-701.

C.C. Danielsen, Thermal Stability of Reconstituted Collagen Fibrils, Shrinkage Characteristics upon In Vitro Maturation, *Mechanisms of Ageing and Development*, vol. 15, pp. 269-278 (1981).

J.S. Dover et al., "Pigmented Guinea Pig Skin Irradiated With Q-Switched Ruby Laser Pulses," *Arch. Dermatol.*, vol. 125, Jan. 1989, pp. 43-49.

L.H. Finkelstein et al., "Epilation of Hair-Bearing Urethral Grafts Using the Neodymium:YAG Surgical Laser," *J. Urology*, vol. 146, pp. 840-842 (1991).

R. Fitzpatrick, "Treatment of Wrinkles with the UltraPulse $CO_2$ Laser," 3 pages in length.

L. Goldman, "Comparison of the Biomedical Effects of the Exposure of Human Tissues to Low and High Energy Lasers," *Ann. N. Y. Acad. Sci.*, vol. 122, May 29, 1965, pp. 802-833.

"Laser Surgery of Angiomas with Special Reference to Port-Wine Angiomas,"*AMA Association*, Jun. 18-22, 1967, 8 pages in length.

J.M. Grevelink et al., "Clinical and Histological Responses of Congenital Melanocytic Nevi After Single Treatment With Q-Switched Lasers," *Arch. Dermatol.*, vol. 133, Mar. 1997, pp. 349-353.

M.D. Grossman et al., "Prospective Evaluation of the Argon Laser in the Treatment of Trichiasis," *Ophthalmic Surgery*, vol. 23, pp. 183-187 (1992).

M.D. Grossman et al., "Experimental Comparison of Laser and Cryosurgical Cilia Destruction," *Ophthalmic Surgery*, vol. 23, pp. 179-182 (1992).

K. Kincade, "Demand for Laser Resurfacing Soars," *Dermatology Times*, vol. 16, No. 10, Oct. 1995, 4 pages in length.

P. Kronick et al., "The Locations of Collagens with Different Thermal Stabilities in Fibrils of Bovine Reticular Dermis," *Connective Tissue Research*, vol. 18, pp. 123-134 (1988).

H. Kubota et al., "Atrial Ablation With an IRK-151 Infrared Coagulator," *Ann. Thoracic Surg.*, vol. 66, pp. 95-100 (1998).

J.G. Kuhns et al., "Laser Injury in Skin," *Laboratory Investigations*, vol. 17, No. 1, pp. 1-13 (1967).

D.B. Kuriloff et al., "Pharyngoesophageal hair growth: The role of laser epilation," *Case Reports*, vol. 98, pp. 342-345 (1988).

J.R. Lloyd et al., "Selective Photothermolysis of the Sebaceous Glands for Acne Treatment," *Lasers in Surgery and Medicine*, vol. 31, pp. 115-120 (2002).

M.A. Mainster, "Ophthalmic applications of infrared lasers—thermal considerations,"*Invest. Ophthalmal. Visual Sci.*, vol. 18, No. 4, Apr. 1979, pp. 414-420.

T. Matsumoto et al., "Ruby Laser Treatment of Melanin Pigmented Skin Lesions using Toshiba Model LRT—301A Ruby Laser," *Journal of the Japanese Society for Laser Surgery and Medicine*, vol. 10, No. 3, Dec. 1989, pp. 451-454.

J.B. Murdoch, *Illumination Engineering—From Edison's Lamp to the Laser*, Chapt. 6.8 entitled "Tungsten-Halogen Lamps," published by Macmillan Publishing Company (1985), pp. 208-211.

M.H. Niemz, *Laser-Tissue Interactions Fundamentals and Applications*, Chapt. 3.2.3 entitled "Heat Effects,"published by Springer-Verlag Berlin Heidelberg (1996), pp. 77-80.

T. Ohshiro et al., "The Ruby and Argon Lasers in the Treatment of Naevi," *Annals Academy of Medicine*, vol. 12, No. 2 (Suppl.), Apr. 1983, 8 pages in length.

T. Ohshiro, "Treatment by Ruby Laser Beams in the Field of Dermatology," "Japan Medical News," Separate Volume No. 2768, issued on May 14, 1997, 21 pages in length (English translation attached).

H. Ohtsuka et al., "Ru Laser Histological Studies and Clinical Experiences of Ruby Laser Treatment," 9 pages in length (1991) (1st page is an English Abstract).

I. Ono et al., "Histopathological Alteration of Skin and Irradiation of Rudy Laser," *Journal of the Japanese Society for Laser Surgery and Medicine*, vol. 11, No. 4, Mar. 4, 1991, 2 pages in length (1st page is an English abstract).

D.Y. Paithankar et al., "Acne Treatment With a 1,450 nm Wavelength Laser and Cryogen Spray Cooling," *Lasers in Surgery and Medicine*, vol. 31, pp. 106-114 (2002).

J.A. Pearce et al., "Kinetic Models of Laser-Tissue Fusion Processes," *Biomed. Sci. Instrum.*, vol. 29, pp. 355-360 (1993).

L.L. Polla et al., "Melanosomes Are a Primary Target of Q-Switched Ruby Laser Irradiation in Guinea Pig Skin," *The Journal of Investigative Dermatology*, vol. 89, No. 3, Sep. 1987, pp. 281-286.

Press Release, "New Laser Eliminates 'Lipstick Bleed,'" 3 pages in length.

J. Ruiz-Esparza et al., "Nonablative Radiofrequency for Active Acne Vulgaris: The use of Deep Dermal Heat in the Treatment of Moderate to Severe Active Acne Vulgaris (Thermotherapy): A Report of 22 Patients," *Dermatol Surg.*, vol. 29, No. 4, Apr. 2003, pp. 333-339.

Spectrum Medical Technologies, Inc., an operator's manual written by Lasermetrics, Inc., exclusively for Spectrum Medical Technologies, Inc., Q-Switched Ruby Laser System Model RD-1200, 23 pages in length.

E.R. Squibb & Sons, "Lasers Light the Way to New Research Concepts in Science Industry Medicine," 33 pages in length.

R. Tanino et al., "Development of Ruby Laser System for Medical Use," *Journal of the Japanese Society for Laser Surgery and Medicine*, vol. 11, No. 4, Mar. 4, 1991, pp. 93-98.

K. Iwasaki et al., (Astract) "Development of Laser Systems for Treatment of Hyperpigmented Skin Lesions," *Publication unknown—entire article is in Japanese except for the Abstract*, revised Mar. 1, 1989, pp. 26-34 (Abstract appears on p. 34).

Brochure by Palomar EsteLux™, "Pulsed-Light System," website http://www.palmed.com/laser_estelux.html, printed Jul. 15, 2003, 3 pages in length.

Brochure by SCITON, "PROFILE™ Combination Long Pulse Erbium and Long Pulse Nd:YAG 1064," website http://www.sciton.com/public/profile.htm, printed Jul. 15, 2003, 2 pages in length.

Brochure by Lumenis Aesthetic, "VascuLight™ The World's Most Versatile System for Aesthetic Procedures," website http://www.aesthetic.lumenis.com/wt/content/vasculaight, printed Jul. 15, 2003, 2 pages in length.

Brochure by Lumenis, "VASCU*Light*™ ELITE [Versatility and Speed for the Ultimate Aesthetic System]," Copyright 2002, the Lumenis group of companies, 2 pages in length.

Brochure by Lumenis, "VASCU*Light*™ VS [Versatility and Speed for the Ultimate Aesthetic System]," Copyright 2002, the Lumenis group of companies, 2 pages in length.

Brochure by Lumenis, "VASCU*Light*™ SR [Versatility and Speed for the Ultimate Aesthetic System]," Copyright 2002, the Lumenis group of companies, 2 pages in length.

\* cited by examiner

SYSTEM AND METHOD FOR FLEXIBLE ARCHITECTURE FOR DERMATOLOGIC TREATMENTS UTILIZING MULTIPLE LIGHT SOURCES

PRIORITY

This application is a continuation of U.S. patent application Ser. No. 10/788,821 filed Feb. 27, 2004 now U.S. Pat. No. 7,326,199, which in turn claims the benefit from U.S. Provisional Patent Application Ser. No. 60/540,981, filed Jan. 30, 2004, entitled SYSTEM AND METHOD FOR FLEXIBLE ARCHITECTURE FOR DERMATOLOGICAL TREATMENTS UTILIZING MULTIPLE LIGHT SOURCES, AND FILAMENT LIGHT SOURCE TO BE USED IN COMBINATION WITH THE SYSTEM AND METHOD FOR FLEXIBLE ARCHITECTURE FOR DERMATOLOGICAL TREATMENTS, which is incorporated herein by reference, and the present application claims benefit from U.S. Provisional Patent Application Ser. No. 60/532,016, filed Dec. 22, 2003, entitled SYSTEM AND METHOD FOR FLEXIBLE ARCHITECTURE FOR DERMATOLOGIC TREATMENTS UTILIZING MULTIPLE LIGHT SOURCES, which is incorporated herein by reference.

FIELD OF THE INVENTION

The present invention relates to a system and method of providing for a range of different dermatologic treatments using different light sources.

BACKGROUND

High power laser and light source medical treatment devices are generally designed with a power supply, light delivery system and user interface which are optimized for the particular type of laser or light source. A consequence is that manufacturers of such systems develop new consoles for each new laser or light source or treatment modality. Systems compatible with multiple light sources generally make major design compromises. A frequent situation is that a multiple modality laser/light treatment platform may be able to provide for different treatments from different light sources, but in general the system will require a number of compromises, such that none of the different light sources are operated in a manner which allows them to provide an optimal treatment for the given light source.

It would be beneficial to provide a system which utilizes different light sources, and has the underlying flexibility in terms of a power supply and user interface and safety features, so that the different light sources can be operated to provide a wide range of different types and levels of treatments.

DETAILED DESCRIPTION

An exemplary embodiment herein provides a dermatologic laser/light source treatment system which provides for a great deal of flexibility with respect to the types of light sources employed. In one embodiment the system provides for a hand piece management unit which provides for holding different hand pieces which provide light treatment from different light sources. Additionally, an embodiment of the system includes a versatile high voltage power supply which allows for the operation of multiple diverse types of light sources. An embodiment of the system herein also includes a detection circuit with sensors (which sense when one of the hand pieces have been removed from holding areas of the hand piece management unit) safety functions and a user interface that allows for easily switching between operation and control of the different light sources.

An embodiment of the system herein includes a flexible and versatile power supply which can drive a wide range of different light sources such as lasers, flash lamps, filament light sources and LEDS, as well as a range of other possible light sources. Further, this power supply can output different amounts of electrical energy and different pulse widths to provide a wide range treatment variations.

In one embodiment a general overview of the design of a system herein would include a main console. This main console could include a frame of aluminum or other material, and side panels, and different components of the system would be secured inside the main console. For example, the main console could house the high voltage power supply for driving the various types of light sources. Coupled to the console are different hand pieces which are used to apply the light treatments to the patient's skin. Depending on the specific light source and design of the system, a light source can be located in the hand piece itself, and electrical current can be delivered to the hand piece to cause the light source to generate light, and a different hand piece could provide for receiving laser light from a laser source which is housed inside the console itself. By providing for the ability to include a laser source secured inside the console, a range of different lasers can be utilized, where it is presently not possible to include certain complex high power laser systems in a relatively small hand piece device.

Figure 1:
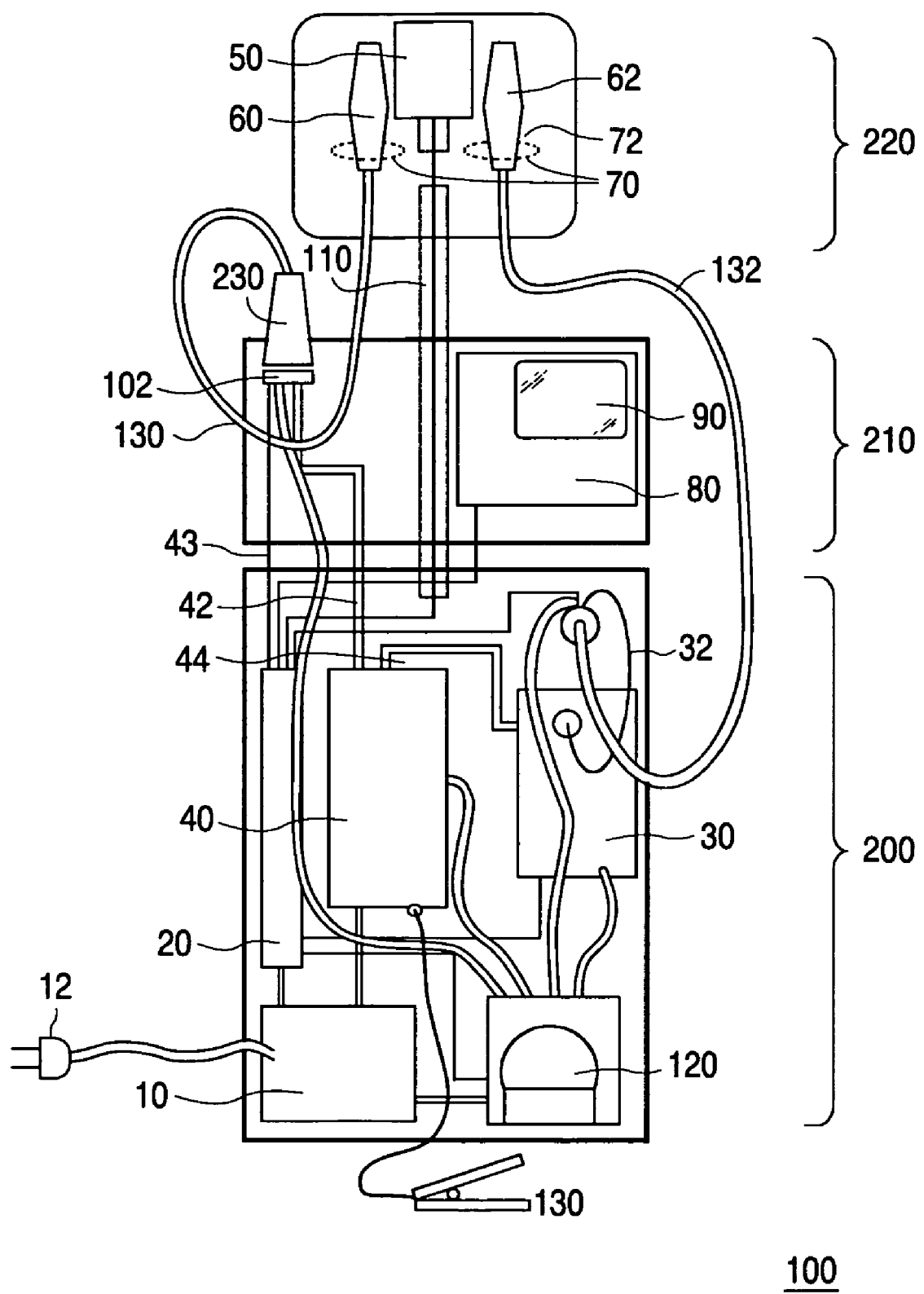
FIG. 1 shows a view of an embodiment of a system herein.

FIG. 1 shows a system 100, which provides a main console 200. Main console 200 houses an AC connection 12 and electrical mains which receives AC power from the AC connection and provides AC and DC power to the other elements of the system. The main console 200 also includes a coolant system 120, where a coolant system would typically include elements such as a coolant reservoir, pump and heat exchanger. Also included is a high voltage power supply (HVPS) 40 which receives electrical energy from the electrical mains 10, and outputs pulses of electrical energy to drive the different light sources. A controller unit 20 which can include a software EEPROM and/or other elements such as a microcontroller, or possibly a programmable CPU, operates as system control electronics. The main console can also include a laser module 30. A user interface module 210 can be provided as an integral part of the main console 200, or it can be a separate module which is coupled with the main console. The user interface module 210 could be implemented using a number of different displays or user interfaces. In one embodiment the user panel could be computer monitor, or a simple LED number display with turn knobs, or other user input devices. In another embodiment, the user interface is implemented using a high resolution touch screen panel 80, such as provided by Sharp Electronics, of Japan with US headquarters at Mahwah, N.J.

The system 100 also includes a hand piece management unit 220. The hand piece management unit can be coupled to the main console 200 by a support member 110, which can be lowered or removed to transport the system 100. The support member 110 can include conducting signal lines where information derived from sensors (discussed in more detail below) in the hand piece management unit 220 can be transmitted to the control unit 20 in the main console 200.

As shown in FIG. 1 two hand pieces 60 and 62 are shown. Depending on the specific types of treatments desired, the system could be designed to allow for more than two hand pieces. Additionally the system can be designed to allow for at least one of the hand pieces to be removed and replaced with a different hand piece which can deliver a different type of light treatment. In the system shown in FIG. 1, the hand piece 60 can provide a first type of light treatment, and the hand piece 62 can provide a different type of light treatment. Further, in the embodiment of FIG. 1 each of the hand pieces mounts in specified storage positions, or holding areas, in the hand piece management unit 220. Additional aspects related to the holding of the hand pieces in the hand piece management unit 220 are discussed below.

The system shown in FIG. 1 provides for a flash lamp disposed in the hand piece device 60, and a laser source 30 in the main console 200 provides laser light energy which is delivered via optic fiber 32 to the hand piece 62. Both the flash lamp and the laser 30 are driven by a flexible pulse-width-modulating high voltage power supply 40. Pending patent application (U.S. application Ser. No. 10/135,981, filed Jan. 27, 2003 DERMATOLOGICAL TREATMENT FLASHLAMP DEVICE & METHOD) which is assigned to the assignee of the present application, and is incorporated herein by reference in its entirety, discloses additional details regarding the operation and design of a suitable HVPS. HVPS 40 includes a current direction control device which allows the power supply to direct electrical energy to either the laser module 30 or an external light source in the hand piece 60.

In one embodiment the HVPS 40 can switch between driving a flash lamp, or other light source, including possibly a small flash lamp pumped laser, located in the hand piece device 60 and driving a laser 30 located in the main console 200, without utilizing a power relay, by utilizing a simmer circuit. In one embodiment both light sources (the laser in the main console and the light source in the hand piece) are driven by a flashlamp. In such an embodiment the light source in the hand piece could be either a small flashlamp driven laser, or the handpiece could provide for emitting light energy directly from the flashlamp to the treatment area. In one embodiment a simmer circuit operates to provide a low amount of electrical power to the light source which is be activated. This low amount of electrical power puts the flash lamp in a mode where it is much less resistive than the other light source which has not received the low amount of current from the simmer circuit. Thus, when the high energy current is supplied by the HVPS, the current is transmitted to the light source which received the input from the simmer current. As an alternative, or in addition, to using a simmer circuit to control which of the light sources is activated, a high power relay could be used to direct the output from the HVPS to one of the different light sources. In one embodiment the operation is such that the control unit, after determining that one of the hand pieces has been removed from the hand piece management unit, will cause the simmer circuit to output low level current to the light source which corresponds to the hand piece which has been removed from the hand piece management unit. Further, the control unit operates such that if both hand pieces are removed from the hand piece management unit, then the control unit will not activate either light source, and will not cause the simmer circuit to output current to either of the light sources.

High power electrical drive currents are conducted from the HVPS 40 via electrical conducting lines 42 or 44, depending on which light source is being driven, or stated differently depending on which treatment modality is active, the driving current will be transmitted by either 42 or 44. A maximum of one light treatment modality is available at a given time. The physical position of the hand pieces 60 and 62 determines which modality may be accessed through the user interface module 210. In one embodiment magnetic sensors embedded in rest positions 70 or 72 send signals to a detection logic circuit 50 located in the hand piece management unit 220. When the hand piece 60 is removed from position 70, the logic circuit 50 will recognize that hand piece 60 is removed, and communicate this the central control unit 20. The control unit 20 will then control the operation of the system 100 such that the HVPS 40 can only drive the light source in the hand piece 60, and HVPS input to the laser module 30 will be disabled. Conversely, if hand piece 62 is removed from position 72, the external light source in the hand piece 62 is disabled and laser module 30 may be enabled. Should both hand pieces 60 and 62 be removed from positions 70 and 72, neither light source will be driven by the HVPS 40. In one embodiment, the user input module 210 will also indicate which hand piece is removed from a seated position in the hand piece management unit 220, and for a hand piece which is removed from the seated position in the management unit 220, the user interface module 210 will allow a user to access controls for the light source which is applied by the removed hand piece. In one embodiment the user interface module 210 includes a user interface device such as a user-controlled touch screen display 90, which is programmed to allow parameter selections only for the modality compatible with the hand piece which is removed from its seated position.

If both hand pieces are removed from the seated positions in the hand piece management unit 220, the touch screen display 90 can indicate that neither light source can be activated. Further aspects of the control of the system by the touch screen 90 are discussed in detail below.

An example of the operation provides that when the hand piece 60 is removed from position 70, the light source in the hand piece 60 can be activated to generate light energy for a treatment application, in response to a user pressing a ready icon on the user interface, which puts the corresponding light source into a ready mode, and the user then steps on the detachable footswitch 230. Similarly when the hand piece 60 is in position 70 and the hand piece 62 is removed from position 72, the laser source 30 can be activated by pressing a ready icon and then stepping on the footswitch 230.

Laser module 30 supplies laser light to hand piece 62 through optical fiber 32 when HVPS 40 applies energy to the laser module 30. Aspects of different potential embodiments of hand pieces for delivering laser light delivered via an optical fiber are shown in U.S. Pat. No. 6,383,176 and U.S. Pat. No. 6,485,484, and both of the patents are incorporated herein by reference in their entirety. Additionally, a cooling fluid from the coolant system 120, control signals to and from control unit 20, and thermo-electric cooler electrical drivelines are routed to laser hand piece 62 through umbilical cable 132. In one embodiment the laser module 30 is an Nd:YAG laser outputting 1064 nm energy. Other flash lamp-pumped, or arc lamp pumped, lasers may be substituted, operating at other wavelengths or laser parameters for providing different dermatologic treatments.

While laser hand piece 62 is designed to deliver laser light which is transmitted via an optic fiber, external hand piece 60 can be configured to deliver flash lamp light or other, even laser, light sources which are mounted inside the hand piece. Cooling fluid from the coolant system 120, high voltage— high current electrical drive lines 42, low voltage thermoelectric cooler electrical lines and control signal lines 43 and various I/O and sensing lines can be routed from the main console 200 to the hand piece 60 through an umbilical cable 130. In one embodiment the hand piece delivers filtered flash lamp light through a contact window. Detailed discussion of some exemplary possible types of such a hand pieces are provided in commonly assigned currently pending patent application (U.S. patent application Ser. No. 10/351,981, filed Jan. 27, 2003 which is incorporated herein). The external hand piece 60 is coupled to the umbilical cable 130 which carries power, coolant and sensing lines, and the connector 230 operates to couple these lines with the elements of the main console 200. This approach of providing a connector 230 and umbilical cable 130 allows a variety of externally generated light sources to be used to apply different types of treatment, without the necessity of replacing the laser module 30 or altering the HVPS 40. Different control operations corresponding to different energy sources in different external hand pieces can be programmed into the control unit 20. A wide range of different light sources could be included in different hand pieces, such additional light sources could include different types of flash or arc lamps for direct lamp treatments, a small flash lamp-driven laser system could also be disposed in a hand piece. Such a design would allow for providing for low powered lasers or for wavelengths that would complement the relatively high powered internal laser module 30. Additionally, non-flash lamp, non-laser sources could be implemented in different versions of hand piece 60, such as filament incandescent lamps, LED arrays, semiconductor diode laser arrays or diode-pumped lasers. The utilization of an HVPS which is able to output a range of different types of driving voltages, and currents, having different pulse widths etc., and the utilization of a flexible and programmable user interface, allows for the addition of a range of different hand pieces.

User detachable hand piece 60 is disconnected from the main console, by unplugging connector 230 from a mating connector 102 of the user interface module 210. Connectors for other hand pieces 60 could be coupled to the connector 102, or a "dummy plug" may be installed to satisfy coolant and electrical interlock or connection requirements for safety and cooling system functioning. Connector 230 contains a non-volatile memory device that contains information for hand piece identification, operational history such as shot history, calibration data, and hand piece configuration data. This non-volatile memory might alternatively be located inside the hand piece itself. The calibration data records can include data from photometric signals from photodetectors in the hand piece 60, where these photodetectors operate to sense the amount of energy output by the light source. By providing a sensing device which directly detects the amount of energy output by the light source, the interchangeable use of hand pieces from one system to another system can be enhanced. Specifically the amount of energy detected allows for slight differences in the electrical drive power from the HVPS of different main consoles to be detected, as these differences are reflected in the amount of energy output by the light source. This ensures that the delivered power or energy is controlled independent of console, and is distinct from simply storing the electrical characteristics of a light-generating hand piece during a calibration step at the factory or by a service technician.

Figure 2A:
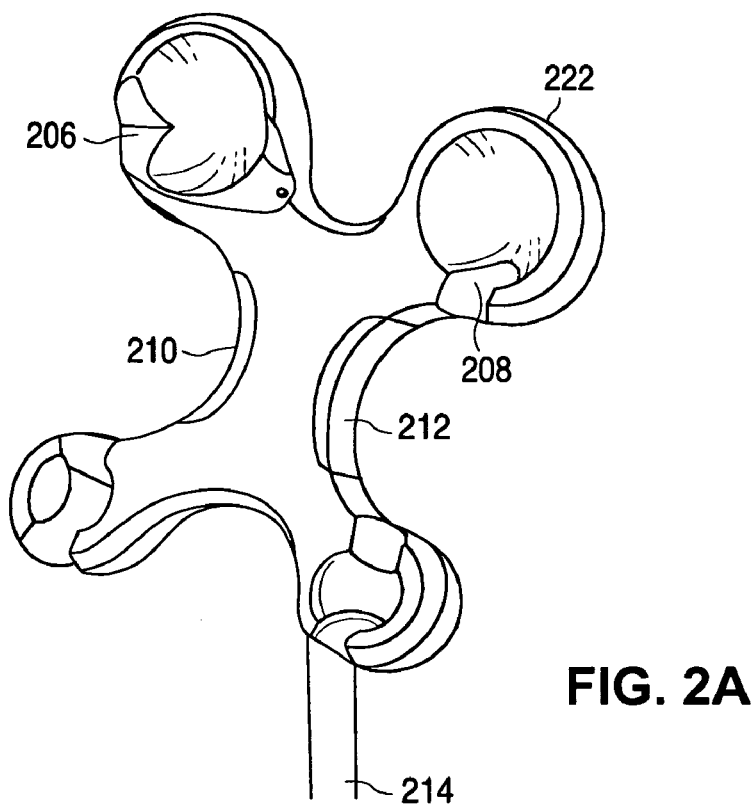
FIG. 2A shows a view of an embodiment of a hand piece management device of a system herein.
Figure 2B:
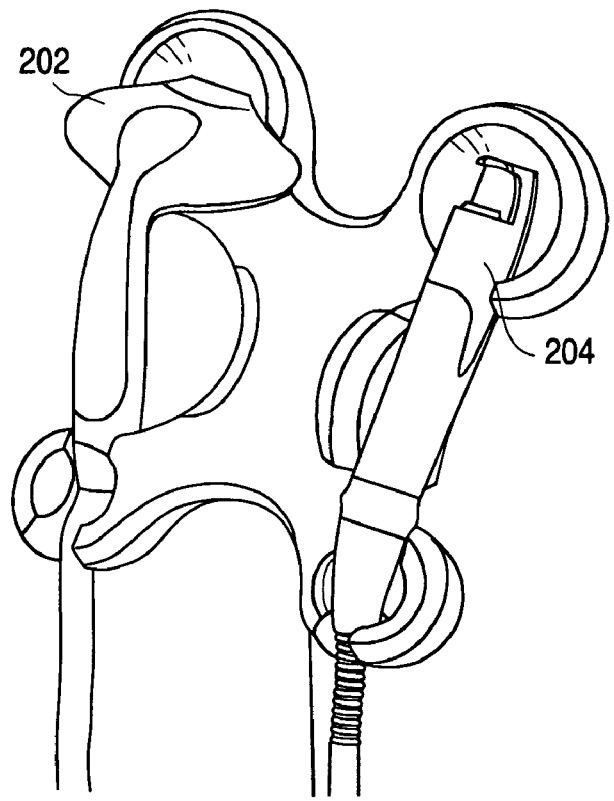
FIG. 2B shows a view of an embodiment of a hand piece management device with hand pieces shown in seated positions.

FIGS. 2A and 2B show views of an embodiment of a hand piece management unit 200. In FIG. 2A the hand piece management unit is shown with no hand pieces seated in the hand piece management unit. In FIG. 2B a hand piece 202 and a second hand piece 204 are shown in seated positions in the hand piece management unit 220. The hand piece management unit has a first receptacle area 206 which is shaped to receive the hand piece 202, so that the hand piece 202 can be seated in the hand piece management unit. The hand piece management unit has a second receptacle are 208 which is shaped to receive the hand piece 204 so that hand piece 204 can be seated in the hand piece management unit 200. Other aspects of the hand piece management unit discussed above in connection with FIG. 1 would be included in the hand piece management unit shown in FIG. 2. For example sensors would be included so that a detection circuit could determine when the hand pieces are seated in the hand piece management unit, and when one or both of the hand pieces are unseated from the hand management unit. The detection circuit would then generate signals which would be transmitted via control lines disposed in the support member 214 to the control unit of the main console to indicate which of the hand pieces are seated in the hand management unit. In addition the hand piece management unit 200 includes indicator lights 210 and 212. When the sensor of the hand piece management unit 200 determines that one of the hand pieces has been removed from the position in the hand management unit 200, the detection circuit will activate the corresponding light to indicate that the removed hand piece is not in its seated position. For example, when hand piece device 204 is removed from the seated in position in area 208 the light 212 will be activated.

The shape of the hand piece device 204 is designed to provide for the delivery of laser light through an optic fiber to a dermatologic treatment area. The shape of the hand piece 202 is designed to among other things accommodate the mounting of light generating source such as for example flash lamps, flash lamp pumped lasers, arc lamps, incandescent lamps, LED arrays, semiconductor (diode) laser arrays, and diode laser pumped lasers.

The modularity of the hand piece design, and the design of the hand piece management unit, the user interface module, and the programming of the control unit and the flexible operation of the HVPS are consistent with providing a platform which can utilize a range of different flash lamp hand pieces. One exemplary user-detachable hand piece includes a filtered xenon flash lamp directed through a temperature controlled sapphire window that contacts the skin for pigmented lesion treatments. The interface between the hand piece and connector on the console allows the supply of high voltage, high current electrical power, coolant flows of several liters per minute, and a number of control and monitoring electrical lines. A "dummy" hand piece allows operation without an actual functioning hand piece connected, in the event that a working hand piece is not available, or is not desired.

The hand piece management unit in operation with the main console and the user interface module provides for intuitive and sophisticated control of functions and treatments, and a range of safety features. For example, in one embodiment if one hand piece is lifted, the user cannot use a user interface touch screen to select the control window for the other hand piece that remains seated in the hand piece management unit. Also, the seated hand piece is disabled so that inadvertently firing it is not possible. Sensors in the hand management unit detect the presence of a seated hand piece. It is not physically possible to mismatch hand piece and mounting position because of the geometric shapes of the hand pieces and the shapes of the seating areas of the hand piece management unit.

Figure 3:
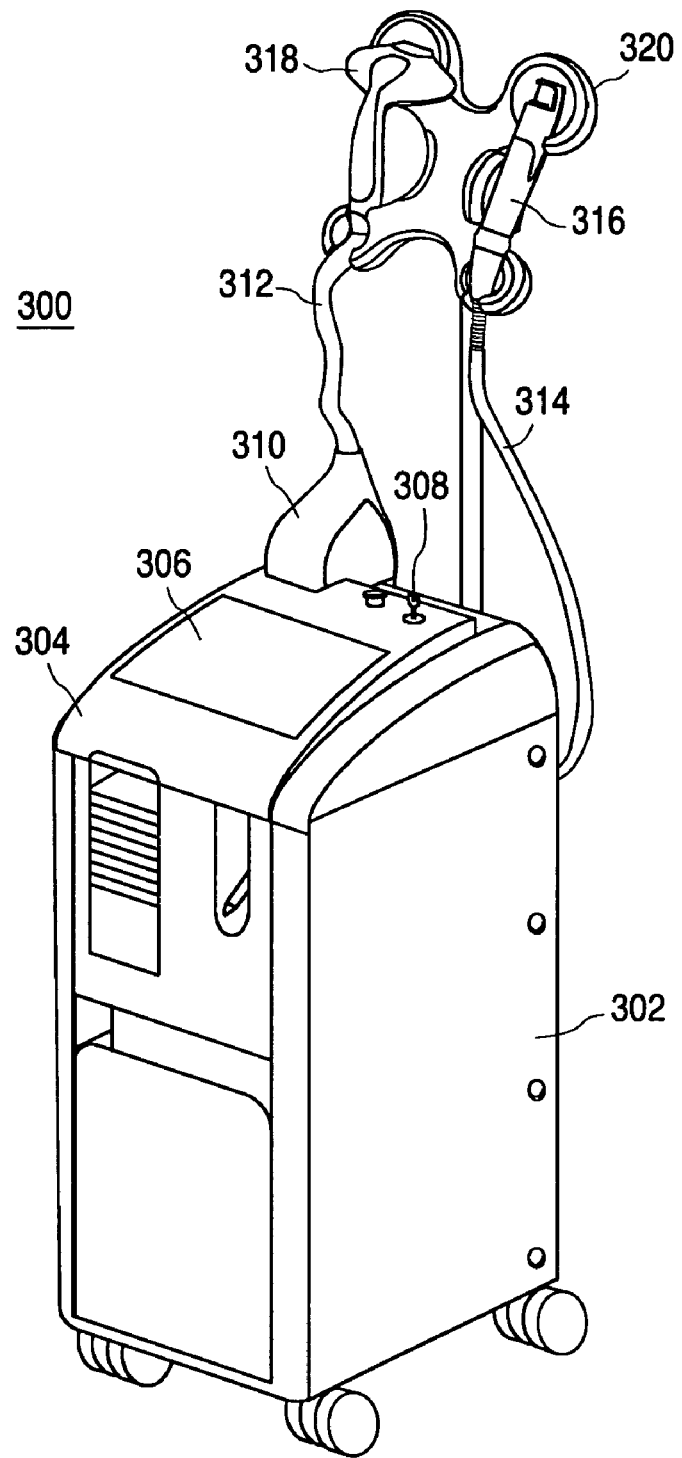
FIG. 3 shows a perspective view of an embodiment of a system herein.

FIG. 3 shows a perspective view an embodiment of a system 300 herein. The main console 302 contains the elements described above in connection with FIG. 1. A user interface module 304 is coupled to the main console 302. In one embodiment a touch screen 306 display is provided in the user interface module. An umbilical cable 314 couples the hand piece 316 to the main console. Another umbilical cable 312 and user detachable connector 310 couple the hand piece 318 with the main console via the user interface module. The user interface panel can also include a key activation element 308, where a user of the system will have to insert a key in order to turn on and power up the system.

Figure 4:
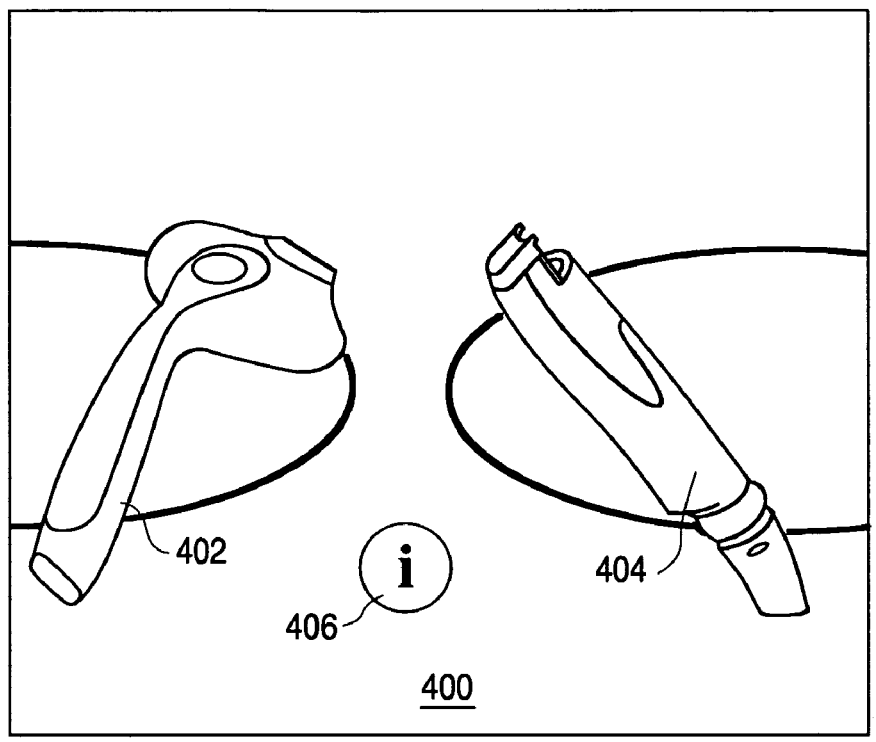
FIG. 4 shows a screenshot from a display of an embodiment herein.
Figure 5:
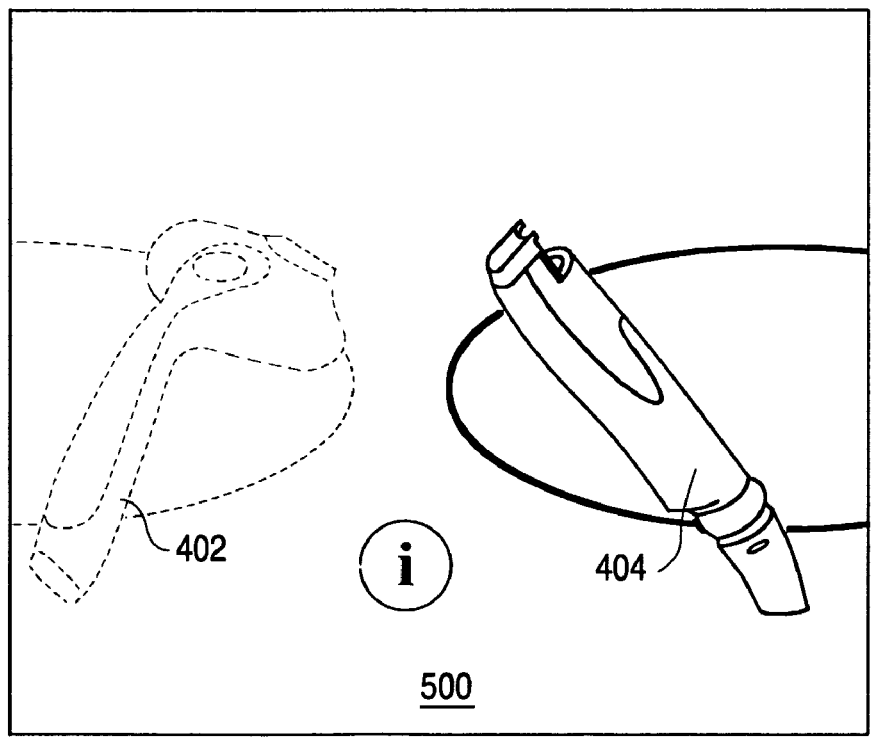
FIG. 5 shows a screenshot from a display of an embodiment herein.

FIGS. 4-10 show exemplary screenshots from a touch screen display 306 which illustrate the operation of an embodiment of a system. FIG. 4 shows a screenshot 400 which shows an icon 402 which corresponds to a hand piece which is shaped to accommodate a light source such as flash lamp. Also shown is an icon 404 which corresponds to the hand piece which delivers laser light from the laser source which is mounted inside of the main console. As will become clear when the screenshot 400 is compared with the screenshot 500 of FIG. 5 for example, both icons 402 and 404 are highlighted, or shown in a manner which indicates that both of the hand pieces in seated positions in the hand piece management unit. Screenshot 500 shows icons 402 and 404, which is similar to screenshot 400, except in screenshot 500 the icon 404 is shown to be highlighted relative to the icon 402. This highlighting of icon 404 relative to icon 402 indicates that the hand piece corresponding to icon 404 has been removed from the seated position in the hand piece management unit, while the hand piece corresponding to icon 402 remains in its seated position.

In this embodiment a user can activate control functions for the light treatments applied by the hand pieces by pressing a finger on a touch screen display position which shows the icon of the hand piece a user desires to control. In screenshot 400, where both icons 402 and 404 are shown as high-lighted, and both of the hand pieces are in the seated, or storage, positions, a user can select to input control instruction for either of the hand piece treatment devices. In screenshot 500 where the hand piece icon 404 is highlighted, which indicates that it has been removed from the seated position, the user can press on the touch screen display at icon 404, and in response to pressing on the icon 404 a control interface for the laser source in mounted in the main console is provided. However, when the icon 404 is highlighted, and the icon 402 is not highlighted, the user will not be able to access the control interface for the hand piece 402. If in response to a screen 500 the user were to select the icon 402, the system could be programmed to either provide no response, or the system could be programmed to indicate to the user that the control of the selected hand piece cannot be accessed while it is in the seated position and the other hand piece is removed from the seated position. By blocking access to the control functions of a hand piece when it is seated and the other hand piece is removed, the risk of a user confusing the control of the two hand pieces is reduced. Thus, the risk of a user inputting controls for the light source of hand piece 404, but then firing the light source of hand piece 402 is significantly reduced.

It should be mentioned that the operation and control of the touch screen could be implemented in a number of different ways, in one embodiment the control unit in the main console would act to provide control over the touch screen display, and to receive and process user input through the touch screen. Further, given that the user detachable hand piece 402 can be switched with an array of other types of hand pieces, the control unit can be programmed to recognize the specific types of hand pieces and light sources which are coupled to the main console, and to generate a user control interface which corresponds to the type of light source which is currently being used.

Figure 6:
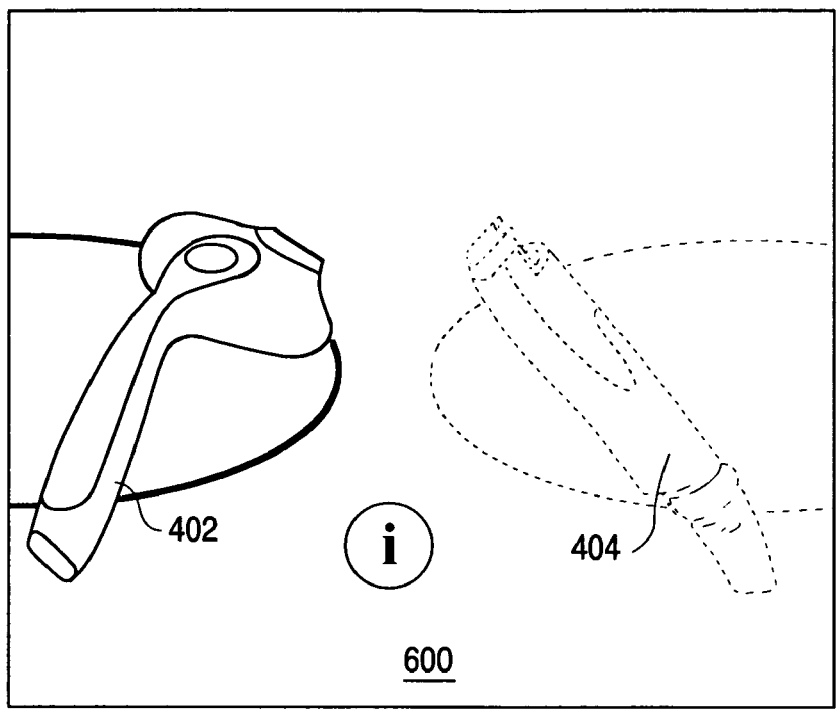
FIG. 6 shows a screenshot from a display of an embodiment herein.

FIG. 6 shows a screenshot 600 which is similar to screenshots 400 and 500, but screenshot 600 corresponds to a situation which the user removable hand piece 402 has been removed from the seated position, and the laser hand piece remains in the seated position. In this situation the icon 402 is highlighted relative to the icon 404. In a manner similar to that described above a user can access a control interface for the device of icon 402 by pressing on the touch screen at a position which corresponds to icon 402.

Figure 10:
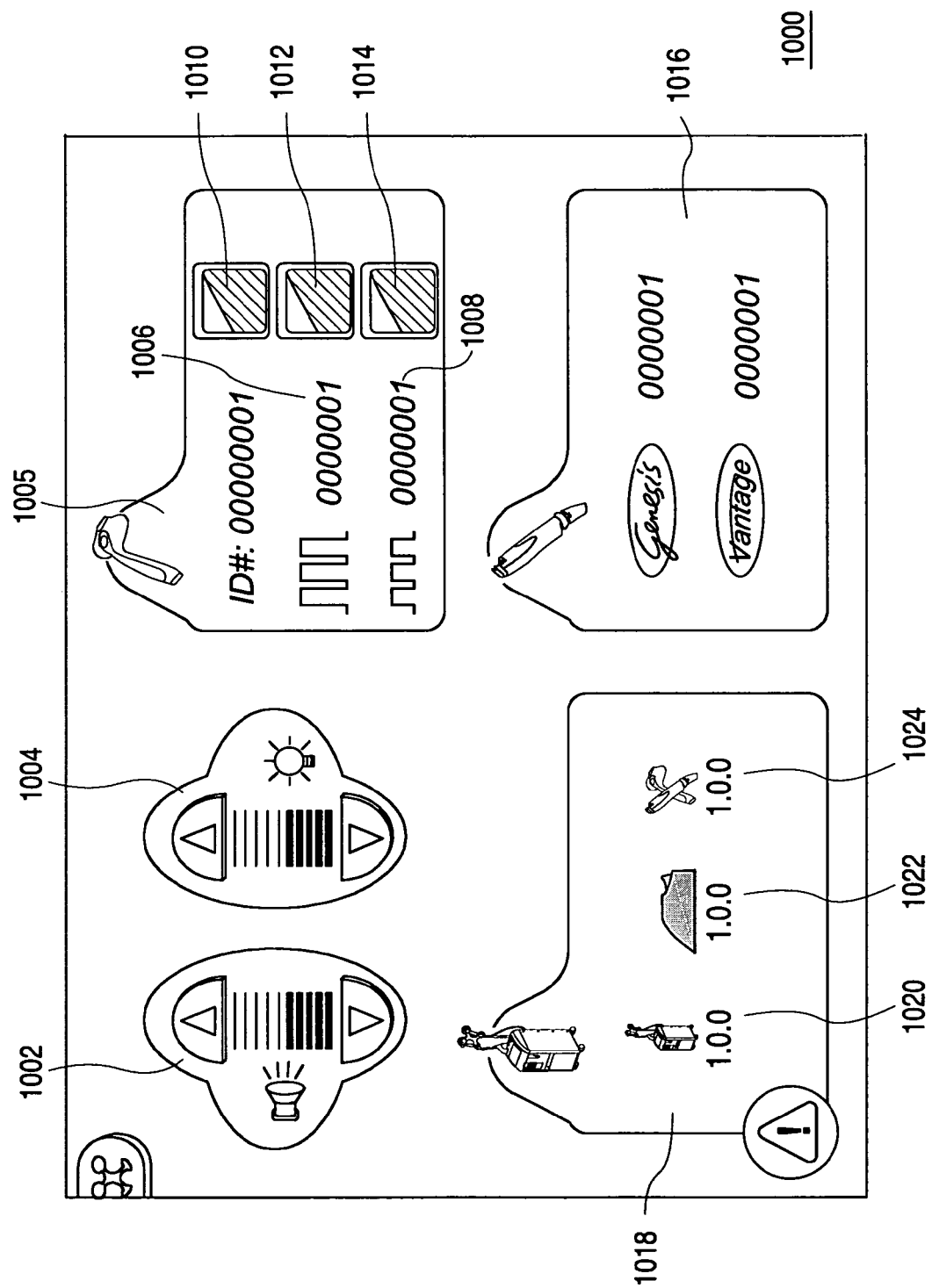
FIG. 10 shows a screenshot from a display of an embodiment herein.

When both of the hand pieces are in the seated position the user can access the control interface for either of the hand pieces, but the user will not be to cause the discharge of the light source from the hand pieces, until one of the desired hand pieces has been removed from its seated position in the hand piece management unit, and the ready control (discussed below) is selected to put the light source in a ready mode. It should also be noted that as shown in each of the screenshots an icon "i" 406 is shown in the screenshots. A user can select this icon by pressing on the touch screen, and in response information about the system and the hand piece devices and their corresponding light sources will be displayed. FIG. 10 shows an exemplary screenshot 1000 of an information screenshot which can be displayed in response to selecting the icon 406, and will be discussed in more detail later.

Figure 7:
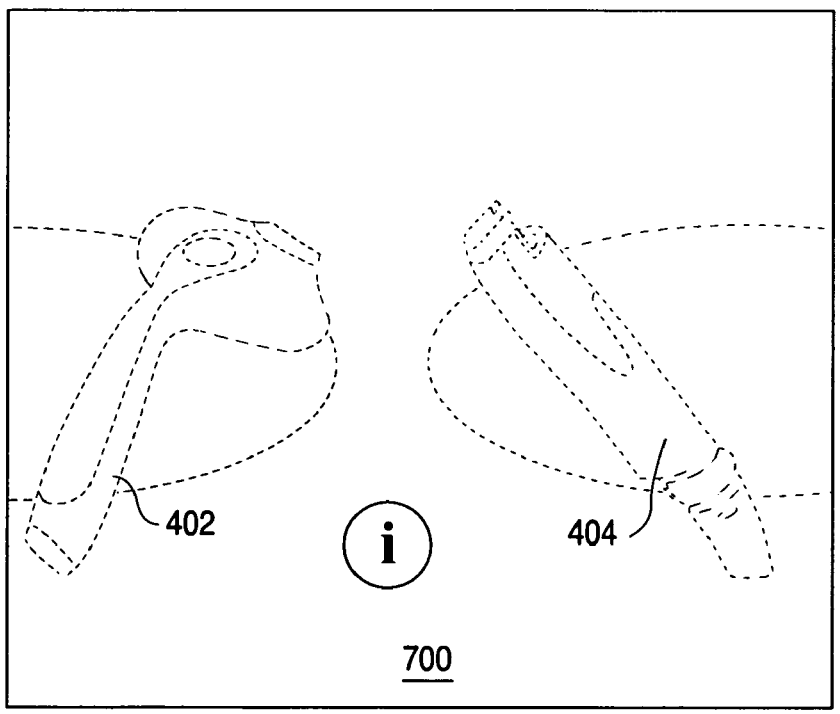
FIG. 7 shows a screenshot from a display of an embodiment herein.

FIG. 7 shows a screenshot 700 where both hand piece icons 402 and 404 are shown as not being highlighted. This screenshot would be displayed in a situation where both hand pieces 402 and 404 have been removed from their seated positions in the hand piece management unit. In this situation a user cannot access the control interface for light sources of either of the hand pieces. Additionally, the control unit of the main console will recognize that both of the hand pieces have been removed from the seated positions in the hand piece management unit, and will prevent the HVPS from driving the light sources for the hand pieces. This operation reduces the risk that would otherwise be present in a situation where a user had removed both hand pieces and then attempted to activate a light source, and might inadvertently activate a light source where the corresponding hand piece is not in a safe position to be activated. For example, the intensity of the generated light could cause an eye injury where a user or patient was looking at the light discharge area.

Figure 8A:
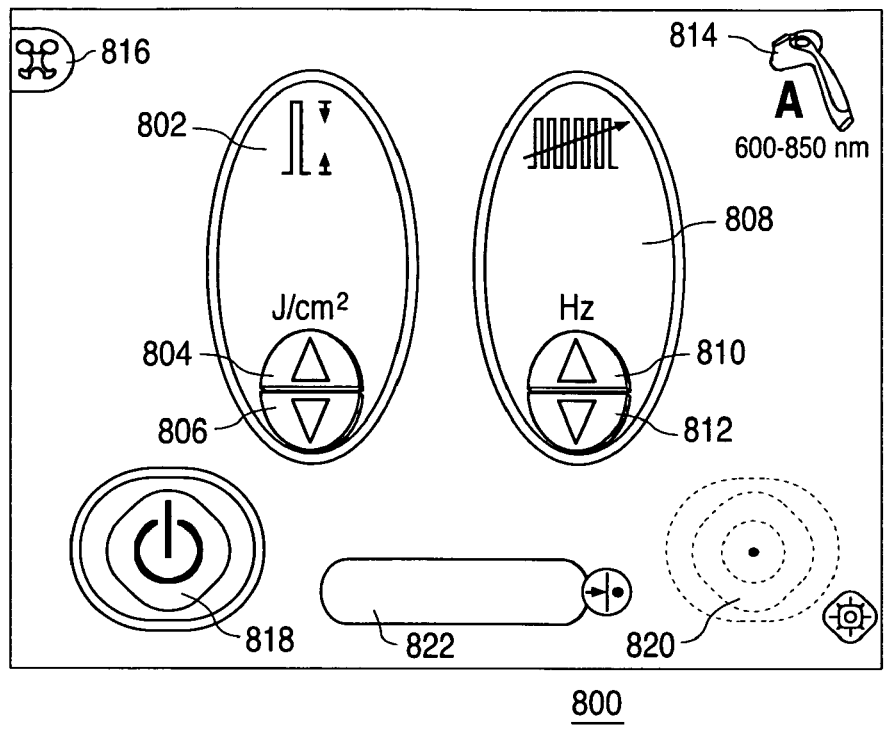
FIGS. 8A-8B show screenshots from a display of an embodiment herein.
Figure 8B:
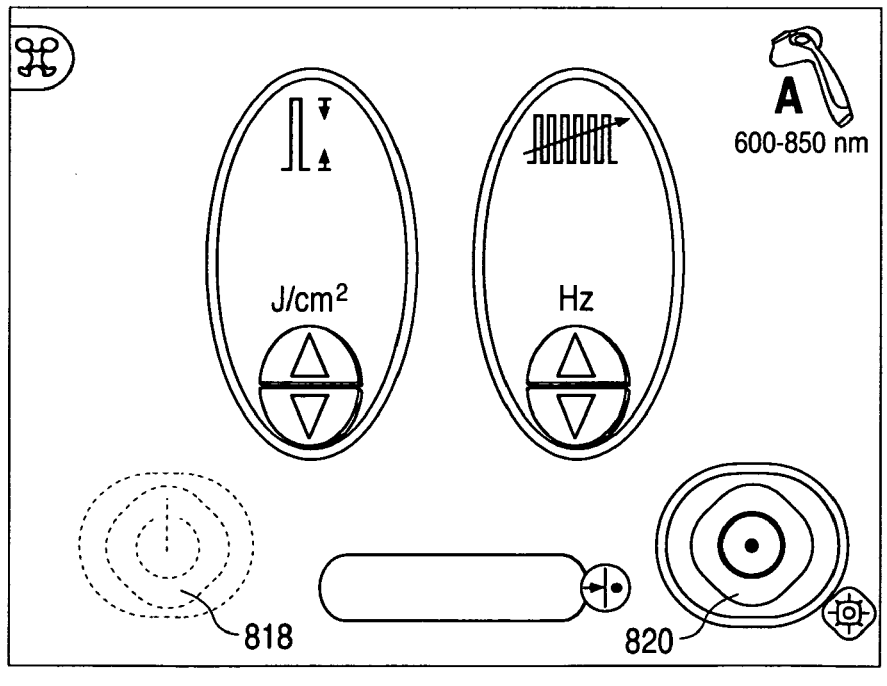

FIGS. 8A-8B show screenshot 800 which corresponds to a user interface for controlling the light source of the removable hand piece 402. In one embodiment this screenshot could be displayed in the situation where the hand piece 402 is removed from the seated position in the hand piece management unit, and the hand piece 404 remains in its seated position, or where both the hand pieces are held in their seated positions in the hand piece management unit, and in either of the these two situations the user presses on the icon corresponding to the hand piece 402. (In the situation where both of the hand pieces are in the seated position, and the user presses on the icon corresponding to the hand piece 402 the ready button icon would be disabled, so that the power supply would not activate the hand piece 402 while it is in the seated position.) In the screenshot 800 the screenshot shows controls for a flash lamp light source positioned in the hand piece. A fluence control area 802 of the screenshot provides up and down arrows 804 and 806 where a user can increase the fluence output by the flash lamp. A pulse repetition rate area 808 provides up and down arrows 810 and 812 where a user can increase or decrease the rate of pulses of light output by the flash lamp. A count area 822 shows the count for the number of exposures which have provided by the flash lamp (this information can be important for system servicing and maintenance). A small hand piece icon 814 is provided in the screenshot 800 to make it intuitively clear to a user as to which hand piece the control interface applies. A return back icon 816 is provided, which allows a user to return to a previous screen by pressing on the icon 816. A standby icon 818 allows a user to put the system in a standby mode by pressing on the standby icon 818. A ready icon 820 allows a user to take the system out of standby mode, by pressing on the ready icon 820. The ready icon 820 would be disabled so that a user could not put the light source for the hand piece in a ready mode, until the hand piece is removed from the hand piece management unit. In response to a user pressing on the ready icon, the standby icon will become unhighlighted, and the ready icon 820 will be highlighted. FIG. 8A shows the screen shot 800 with the system in a standby mode, and FIG. 8B shows the screen shot 800 with the ready icon 820 highlighted, which indicates that the system light source is now ready to be activated by stepping on the foot switch. Initially the system will need to prepare to provide power to the light source; once the system is ready to drive the light source, the ready icon can change color, for example, it could change from yellow to green. At this point if the user steps on the activation pedal the HVPS will drive the flash lamp according to the input parameters shown in the screenshot 800.

Figure 9A:
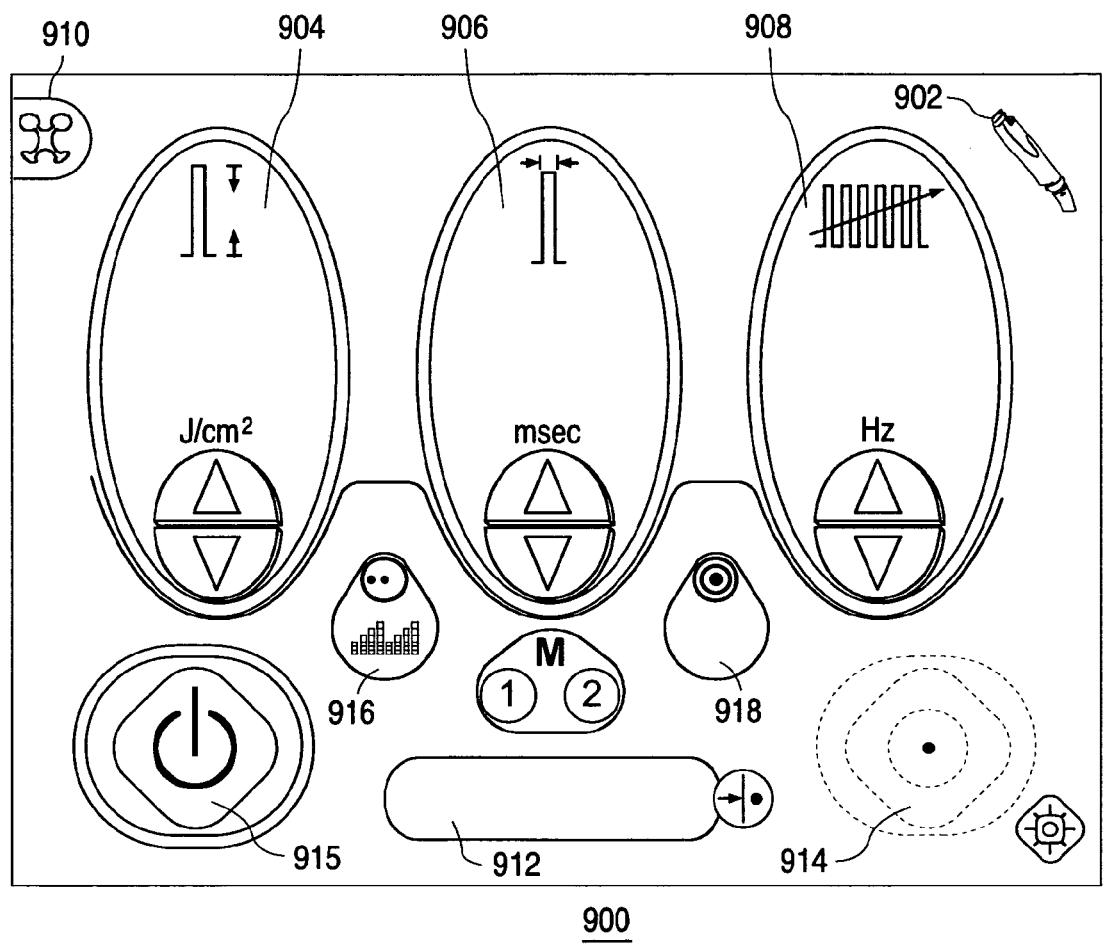
FIG. 9A-9B show screenshots from a display of an embodiment herein.
Figure 9B:
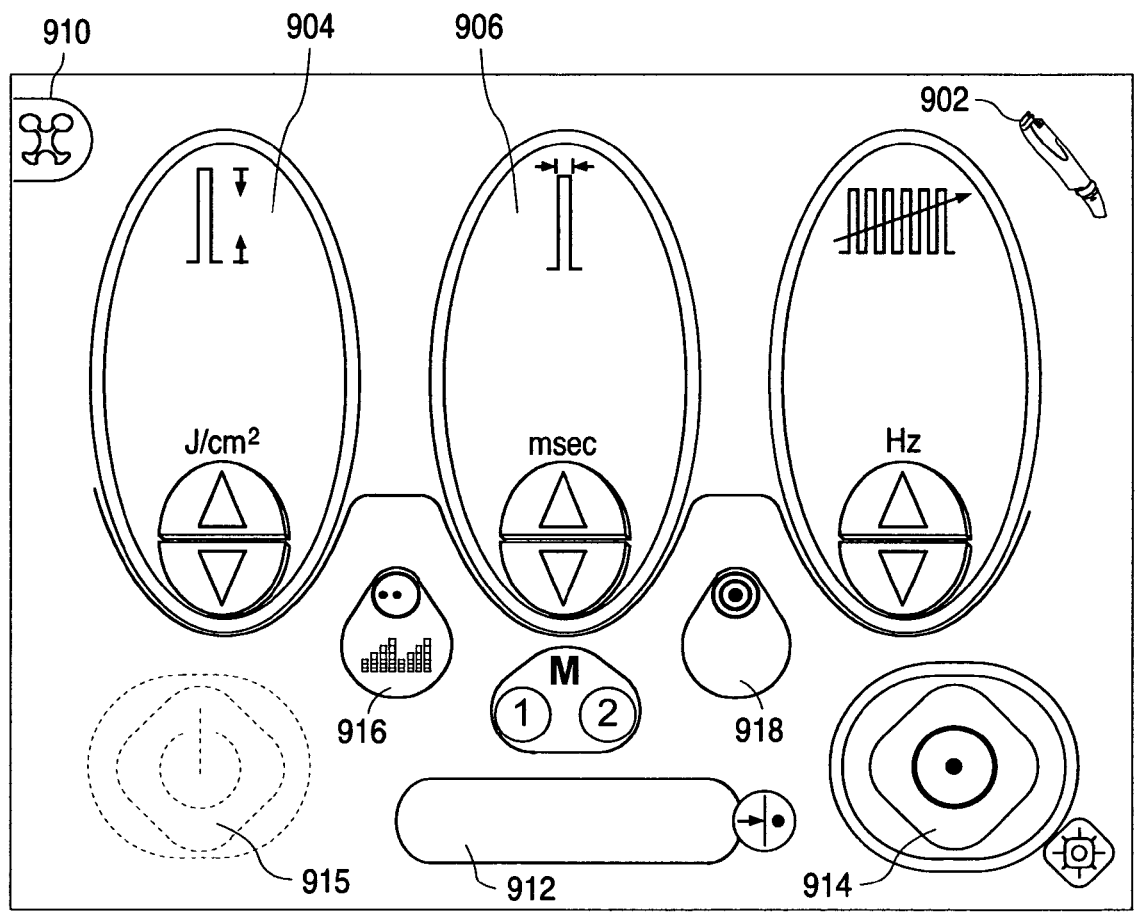

FIGS. 9A-9B show a screenshot 900 where a user has pressed on hand piece icon 404 when the hand piece 404 has been removed from its seated position in the hand piece management unit, or when both hand pieces are in their seated positions in the hand piece management unit. The screenshot 900 provides a control interface for the laser light source disposed in the main console. The screenshot 900 shows an icon 902 which corresponds to the hand piece which delivers light from the laser light source in the main console. The screenshot 900 provides a fluence control area 904 with up and down arrows where a user can increase or decrease the fluence by pressing on the up and down arrows. A pulse width control area 906 provides up and down arrows where a user can increase or decrease the pulse width by pressing on the up and down arrows. A pulse frequency control area 908 provides up and down arrows where a user can increase or decrease the frequency of light exposures output by the laser source. The screenshot 900 also provides a return back icon 910, a exposure count area 912, a ready icon 914, and a standby icon 915 which operate in a manner similar to that described in connection with FIG. 8. FIG. 9A shows the screen shot with the 915 standby icon highlighted, which indicates that the system is in standby mode, and FIG. 9B shows the screen shot with ready icon 914 highlighted which indicates that the system is in a ready mode. Additionally, screenshot 900 provides an aim control mode area 916. In one embodiment the hand piece 404 which delivers energy from the laser source provides an aiming guide light which shows the user the position on the patient's skin where the laser light will be applied. The aiming guide light can be operated at different intensity levels, and can be operated in an intermittent or continuous mode. The screenshot 900 also provides a spot size control area 918 where a user can select different spot sizes for the laser light which is applied to the patient during treatment.

FIG. 10 shows a screenshot 1000 which can be displayed in response to a user pressing on the information icon 406 which is shown in screenshot 400 for example. Screenshot 1000, provides a speaker volume control area for the system 1002, where the user can increase or decrease the volume of sound coming from speakers which could be included in the system. A screen intensity control area 1004 allows the user to control the screen display intensity. A removable hand piece display information area 1005 shows information about the removable hand piece. This information can include an identification number or serial number for the hand piece. This information can also include an area 1006 showing the number of high fluence exposures which have been generated by the light source in hand piece. The information can also include an area 1008 showing the number of low fluence exposures which have been generated by the light source in hand piece.

The removable hand piece information area 1005 can also include icons which indicate the number of different types of treatment which are possible using the different types of possible removable hand pieces. For example where pigment icon 1010 is highlighted, this would indicate that the removable hand piece connected to the system is suitable for providing pigment treatment. Where hair icon 1012 is highlighted, this would indicate that the removable hand piece connected to the system is suitable for providing hair removal treatment. Where vascular icon 1014 is highlighted, this would indicate that the removable hand piece connected to the system is suitable for providing vascular treatment. A laser hand piece device information area 1016 provides information showing the number of exposures delivered by the laser in the main console, under different operating modes.

General system information area 1018 provides information showing information about different elements of the system. For example, icon 1020 shows that the programming of the control unit of the main console corresponds to version 1.0.0; icon 1022 shows that the version of the user interface module is 1.0.0; and icon 1024 shows that the programming for controlling a cooling loop of the handpieces.

Figure 11:
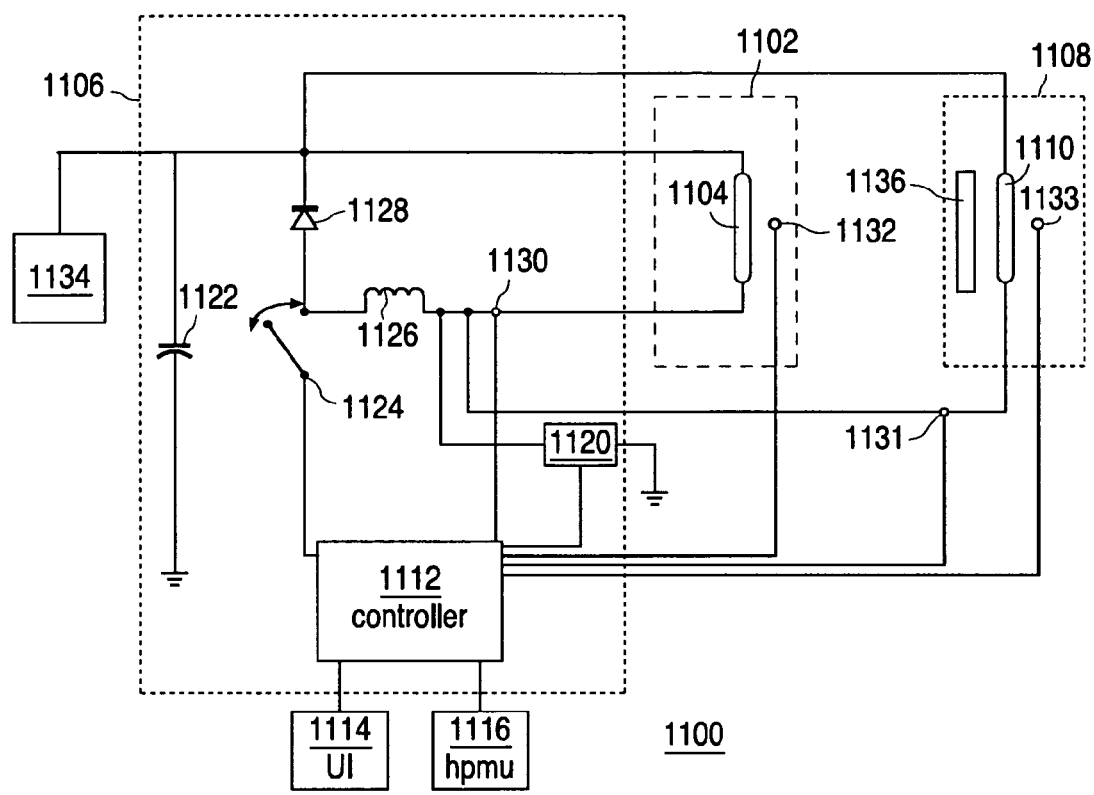
FIG. 11 shows an embodiment of a system herein.

FIG. 11 illustrates a system 1100 an embodiment herein. As shown a power supply 1106 is coupled with two different light sources 1104 and 1110. In one embodiment the power supply uses a controlled chopper circuit with an inductive filter element 1126, operating in a pulse width modulated controlled current mode (in which the current is controlled and the voltage is determined by the device impedance and the impedance of the filter). Power supply 1106 could be also operated in a pulse width modulated controlled voltage mode (in which the voltage is controlled and the current is not controlled) or in a controlled power mode (in which the voltage and/or current are controlled in a manner resulting in controlled power).

As shown system 1100 illustrates a situation where a removable hand piece 1102 having a flashlamp 1104 is coupled to main console and the power supply 1106, and when activated removable hand piece applies energy from the flashlamp 1104 to the patient's skin. The system also includes a high power laser 1108 which can be housed in the main console as discussed above. As is known, lasers such as Nd:YAG lasers can be driven by a flashlamp. The high power laser 1108 includes a flashlamp 1110 and other components 1136, such as optical components which operate to generate and output coherent light in response to light output by the flashlamp. Indeed, dedicated chopper circuit power supplies have in the past been used to drive flashlamp pumped lasers. However, the design of an embodiment herein offers significant advantages over prior systems in that it provides the ability to control the power supply such that a single power supply is coupled with multiple light sources, and operated to provide for a wide range of different electrical pulses for different light sources, and to recognized which type of light source connected, and to direct electrical energy to a selected light source. An embodiment herein offers advantages in that it allows for a system with a single power supply to operate numerous light sources providing a variety of different treatments. In an embodiment herein, the controller of the power supply 1112 receives signals originating from the user interface 1114 and sensors in the hand piece management unit 1116 and based on these signals determine which flashlamp should be driven when a user initiates the activation of the power supply.

The operation of the power supply will be described in the context of the situation where a user has removed the removable handpiece 1102 from the hand piece management unit, and initiated the activation of the light source of the removable hand piece. In this situation when the hand piece 1102 is removed from the hand piece management unit, and put it in ready mode, the controller 1112 will cause the simmer circuit 1120 to put the light source 1104 in an operational conductive mode, and the flashlamp 1110 of the higher power laser 1108 will remain in a highly resistive mode, as discussed above. Alternatively, or in addition, see discussion of FIG. 16 below, a high power switch or relay could be used to direct energy to the selected light source.

The energy storage capacitor 1122 is charged by the main electrical supply 1134 to a level allowing the desired energy to be delivered without unacceptable lamp voltage droop, where driving the flashlamp, at the desired current. When switch 1124 is closed current ramps up current through lamp 1104, inductor 1126, and switch 1124. When the appropriate current is reached, the controller 1112 opens the switch 1124 and the current now diverts to the diode 1128. When the current flow decays to an appropriate level (typically 75% of the peak value) the controller 1112 again turns on the switch 1124 and the cycle repeats until a pulse is complete.

Figure 12:
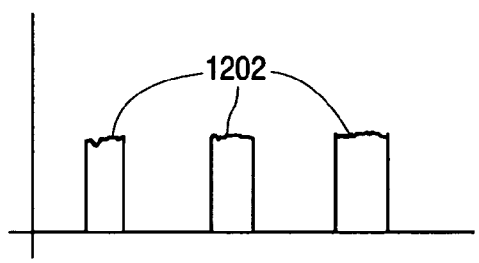
FIG. 12 shows pulses of light energy output by a flashlamp of an embodiment herein.

This toggling of switch 1124 on and off during a single pulse 1202 creates a slight ripple in pulse 1202 as indicated in FIG. 12. The operation of the power supply 1106 in a controlled power mode refers to both the electrical energy delivered to lamp 1104 and the resulting controlled optical power from lamp 1104. Current sensor 1130 and photodiode 1132 can be used independently or in concert to control the optical power delivered to skin. A current sensor 1131 and photodiode 1133 can also be provided for controlling the operation of the power supply when it is driving the flashlamp 1102 of the high power laser 1108. The treatment waveform of the optical energy created by lamp 1104 corresponds generally to the waveform of the electrical energy delivered by power supply 1106 to lamp 1104.

Lamp life can be a concern in high energy flashlamp systems. Instead of using a treatment waveform comprising one large pulse tens of milliseconds long, according to an embodiment herein, the power supply 1106 can modulate the lamp power in such a manner that the treatment waveform comprises many shorter, high power, but relatively low energy, pulses with small gaps between them. The gaps decrease the maximum thermal load and plasma discharge wall loading power by allowing the plasma to thermally relax between each shorter pulse. This reduced loading should result in longer lamp life. For example, instead of supplying a flashlamp with a treatment waveform comprising a single pulse 15-20 ms long, the flashlamp can be supplied with, for example, a treatment waveform comprising one or more of the following power pulse sequences: 8 power pulses each 2 ms long separated gaps approximately 0.6 ms long; 4 power pulses each 4 ms long separated gaps 0.75 ms long; 16 power pulses each 1 ms long separated gaps 0.25 ms long; 2 power pulses each 9 ms long separated gaps 2 ms long. In addition, a power pulse sequence may include power pulses of different durations separated by the same or different length gaps or of power pulses of equal durations separated by different length gaps.

In the present invention, the controllable power supply using the switch, allows for current controlled operation of a light source. In current controlled operation, the power supply operates to control the amount of current, and allows for a range of different flashlamps to be used, where the power supply can adjust its operation to supply a desired amount of current for the flashlamp; thus a range of different flashlamps having different impedance values can be use, as the lamp does not determine the amount of current that the power supply will deliver to the lamp. This has several consequences: A short flashlamp arc length (or any other length) relative to the aperture length can be used, thereby matching the desired treatment type and size, with attendant increase in electrical-to-optical efficiency, a reduced stored energy requirement, and a more ergonomic handpiece design through a reduction in the required lamp dimensions. Further, the flexibility of the power supply allows for development of different handpieces having different sizes, and apertures, and using a range of different types of light sources, including a range of different types of flashlamps.

The ability to control the power allows for a wide range of pulse amplitudes and widths. Arbitrary waveform generation is possible using power supply 1106 but is not possible with PFN (a pulse forming network) or RDC (reservoir discharge) circuits. The range over which arbitrary lamp currents can be set with the power supply is typically 10:1, which can be selected within one pulse. RDC circuits can only set up for one current during a pulse and must accept the voltage and current droop associated with energy depletion of the storage capacitor. Capacitor voltage drops do not affect output power as in the RDC circuit. This allows constant power pulses 1202 to be generated with less stored energy. In a preferred design the capacitor voltage can drop by 50% before output power is affected at all. In a typical RDC design a capacitor voltage drop of 50% results in an 87% reduction in output peak power.

Figure 13:
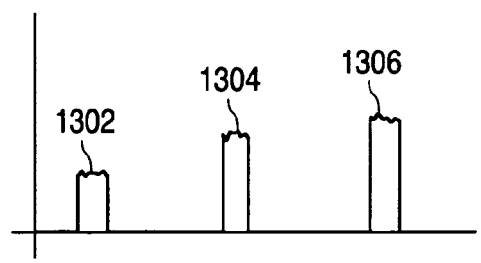
FIG. 13 shows pulses of light energy output by a flashlamp of an embodiment herein.

FIG. 13 illustrates a treatment waveform comprising an arbitrary pulse train, consisting of several pulses 1302, 1304, 1306 of selected amplitudes, durations, intervals etc., to achieve the most effective treatment. In this example, successive pulses increase in amplitude in a potentially useful therapeutic treatment. Some pulse widths and constant or near-constant pulse amplitude (light intensity) combinations can be achieved with a controlled current source, such as power supply 1106, that the PFN and RDC circuits either cannot achieve or require an impractical or uneconomical energy storage bank. For example in one embodiment, pulse widths >5 ms in combination with fluences in the >10 J/cm2 range are achievable with power supply 1106.

Different removable hand pieces 1102 can be used, by coupling different hand pieces to the connector of main console as described above. The removable hand piece to be connected can be selected according to the particular procedure to be conducted and the width (dimension) of the treatment area. Using the user interface, the user may input one or more parameters, such as pulse width or widths, the optical fluence for each pulse, the period between pulses (which may be the same or different), the number of pulses delivered each time foot switch is depressed, and pulse shape, etc. As discussed above, power supply 1106 of assembly of the system 1100 can be a chopper circuit with an inductive filter operating as a pulse width modulated current supply, and may also operate as a pulse width modulated optical power regulated supply.

In one embodiment, the waveform selected may have a generally constant current value equivalent to an optical fluence of at least about 1 J/cm2 (such as for narrow notch filter treatment of superficial lentigines in heavily pigmented skin) or at least about 4 J/cm2 (such as for lighter skin) or at least about 10 J/cm2 (such as for light lentigines in light skin). Also, a specific spectral range may influence the optical fluence so that, for example, the optical fluence for the output light treatment hand piece embodiment would typically not go above about 10 J/cm2 and the long wavelength pass embodiment would typically not be used below about 3 J/cm2. The waveform selected may also have a generally constant current value equivalent to an optical peak power producing a total fluence of between about 2 and 50 J/cm2. The waveform selected may have a generally constant current value equivalent to an optical fluence of at least about 10 J/cm2 with a pulse width of at least about 5 ms. The waveform may be selected to have a generally constant current value with a pulse width of about 1 to 300 ms, or about 5 to 50 ms, or about 10 to 30 ms. The waveform selected may have a generally constant current value and may be substantially independent of pulse width and repetition rate. The settings will depend upon various factors including the type of treatment, the size of the lesion, the degree of pigmentation in the target lesion, the skin color or phototype of the patient, the location of the lesion, and the patient's pain threshold. Some or all of the operational parameters may be-pre-set and not be user-settable. In particular, the bandwidth spectrum, such as 590-1100 nm, 590-850 nm, and 590-700 nm, will generally be fixed for a particular removable handpiece. However, it may be possible to construct a handpiece so that appropriate wavelength filters and reflectors may be changed by the user to change the wavelength of the output radiation.

The above discussion illustrates the advantages of using a highly controllable power supply to drive a variety of different removable flashlamp or laser handpieces. However, it should be recognized that further advantageous are obtained using such a power supply. For, example, consider the situation where a user has the removable hand piece seated in the hand piece management module, and removes the second hand piece which delivers light from the high power laser 1108, and puts the high power laser in ready mode. In this situation the controller 1112 will receive signals originating from sensors in the hand piece management unit 1116 and the user interface 1114, and in response to these signals put the simmer circuit 1120 and flashlamp driving the high power laser 1108 in to an operating conductive mode, and the light source in the removable hand piece will be in a nonoperative mode. The power supply 1106 can then control provide energy to drive the flashlamp of the high power laser. In this situation the parameters of the electrical energy can be controlled so that they provide for optimum operation of the high power laser for the specific treatment being applied.

Additionally, the controllable power supply is operable to drive other types of light sources which can be supplied in different removable handpieces. For example, one additional hand piece includes a filament light source which is suited for outputting a broad range of electromagnetic energy including near infrared and infrared energy which is difficult to achieve with flashlamps. This infrared and near infrared energy is useful for providing treatments such as collagen shrinkage through dermal heating. Additional aspects of hand piece using a filament light source are described in U.S. Provisional Patent Application No. 60/497,745 filed Aug. 25, 2003, entitled, OPTICAL DEVICE FOR HEATING SKIN USING NIR LIGHT TO PRODUCE TISSUE SHRINKAGE, which is incorporated herein by reference in its entirety.

Figure 15A:
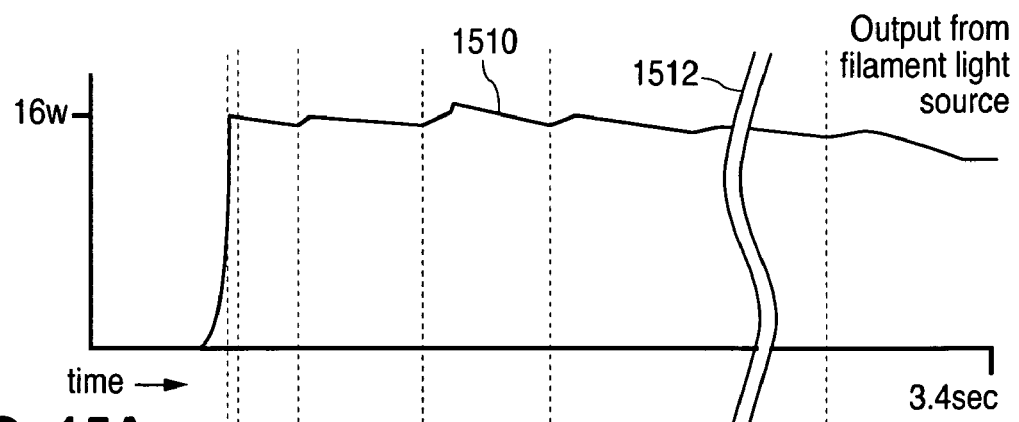
FIG. 15 shows a current applied to a filament light source, and power output by a filament light source.
Figure 15B:
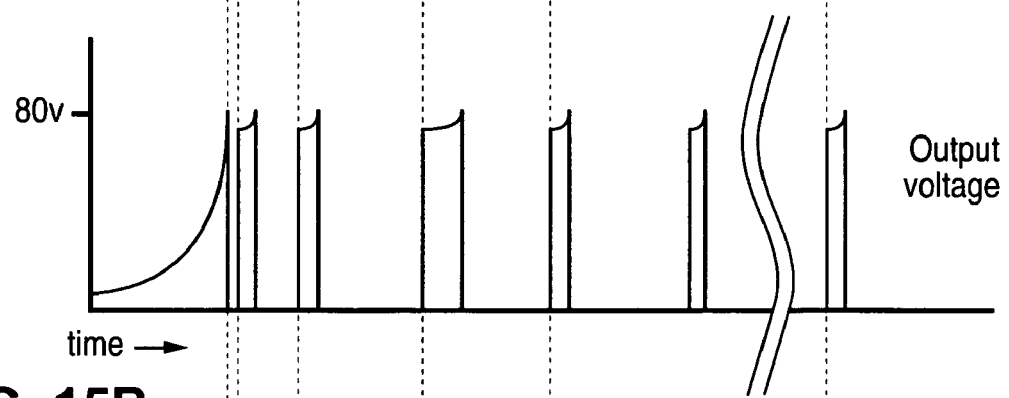
Figure 15C:
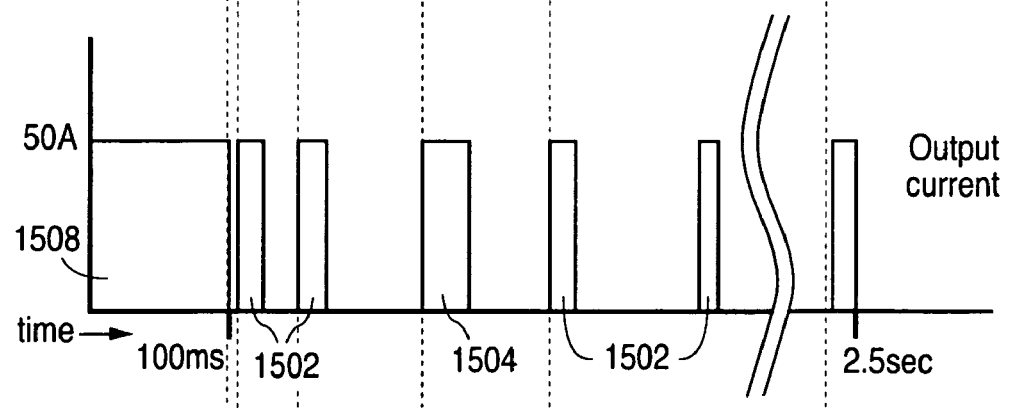
Figure 17:
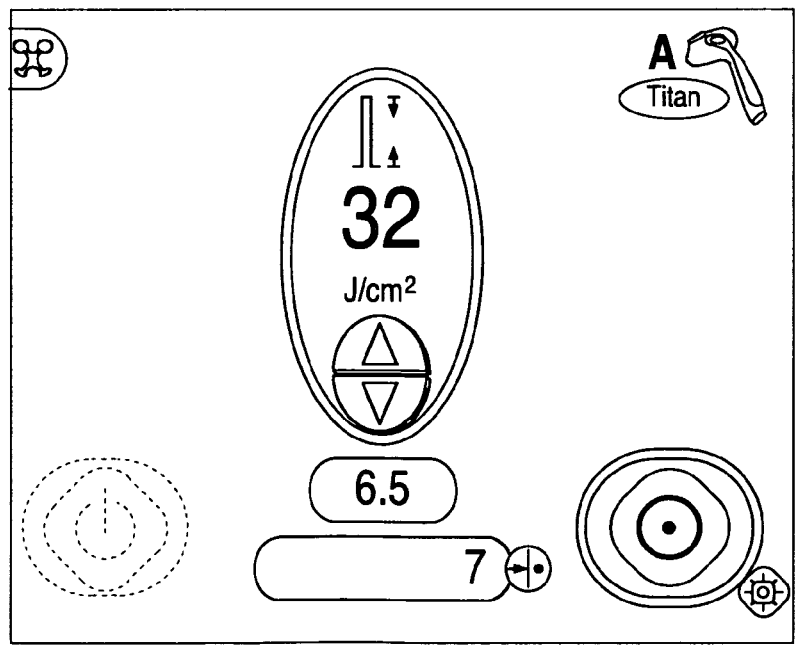
FIG. 17 shows screen shot from a display of an embodiment herein.

The general operation of the system is that the user would remove the hand piece with the filament light source, and the user interface would display a screen which allows the user to input a total amount of fluence for a treatment exposure. An example of such a screen 1700 is shown in FIG. 17. The controller would then determine a total length for a treatment exposure, and then control the power supply to drive the filament lamp for an appropriate amount of time. In driving the filament light source pulses of electrical current are applied to the filament light source which are of different amplitude and duration than the pulses which are used to drive flashlamps. FIG. 15 shows the current output for driving a filament light source, and the corresponding power output 1510 by the filament light source, which would be disposed in a removable handpiece in one embodiment herein. In this example a filament light source would be driven with an initial pulse 1508 of electrical current having a duration of 100 ms, and an current amplitude of 50 A, and then subsequent pulses 1502 and 1504 of electrical current having a pulse widths of 1-2 ms. Of course depending on the desired operation of the system pulse widths of greater or less than 1-2 ms could also be used, and the frequency of the pulses could be increased or decreased. The long initial pulse 1508 is used to initially heat the filament light source. Rather than an initial long pulse, a series of relatively closely spaced short pulses could also be used to initially heat the filament. Pulses 1502 show 1 ms pulses and 1504 shows a 2 ms pulse, the duration between pulses can be varied based on a signal from a photodetector which would sense the output power of the energy output by the filament light source. In one embodiment for example the applied electrical pulse would be such the output of power from the filament light would be ±1.5% of 16 watts. Thus, when the photodector sensed the power output dropped to a threshold level a 1 ms pulse of 50 A would be applied to the filament light source. As shown in FIG. 15 each pulse of current would have result in a corresponding voltage applied to the filament light source. The output power from the filament light source is shown in FIG. 15 as detected by a photodetector as curve 1510. The area 1512 is a break in the time line, during which additional pulses would continue to be applied to the filament light source. The operation of the filament light source is such that it will continue to output electromagnetic energy for so long as the filament remains sufficiently hot. Thus, the curve 1510 shows that optical power continues to be output by the filament light source even after the pulses of electrical current are no longer being supplied to the filament light source. In the example, shown in FIG. 15 for example where the last electrical pulse is applied at 2.5 seconds, the filament light source would continue to output a significant amount of output power up to about 3.4 seconds.

The above described operation of the power supply driving a filament light source, illustrates an aspect of an embodiment of the present system. Specifically, a filament light source is normally considered a relatively low current, low voltage device. However, the filament light source can be driven with the same power supply which is used to supply high current and high voltage that is required to drive a flashlamp. As described above the ability to control the power supply to short pulses of relatively high current, allows for the controllable power supply to drive the filament light source in a manner for providing effective treatments.

The filament can also be driven continuously by a supply, it is not a requirement to pulse the filament current at intervals during the treatment. This was actually a method developed to obtain filament capability using the same power supply that drives flashlamps. Other variations and different methods could be utilized such as providing a higher current during the preheat phase of the pulse, in order to bring the lamp up to heat quickly. This could be combined into one long pulse with higher current in the beginning and lower current at the end. An alternate control method would be to control the voltage applied to the lamp. The voltage would ramp up at a controlled rate to limit the inrush current. Alternately the voltage control would be a step applied and the current limit of the supply would limit the current.

Figure 14:
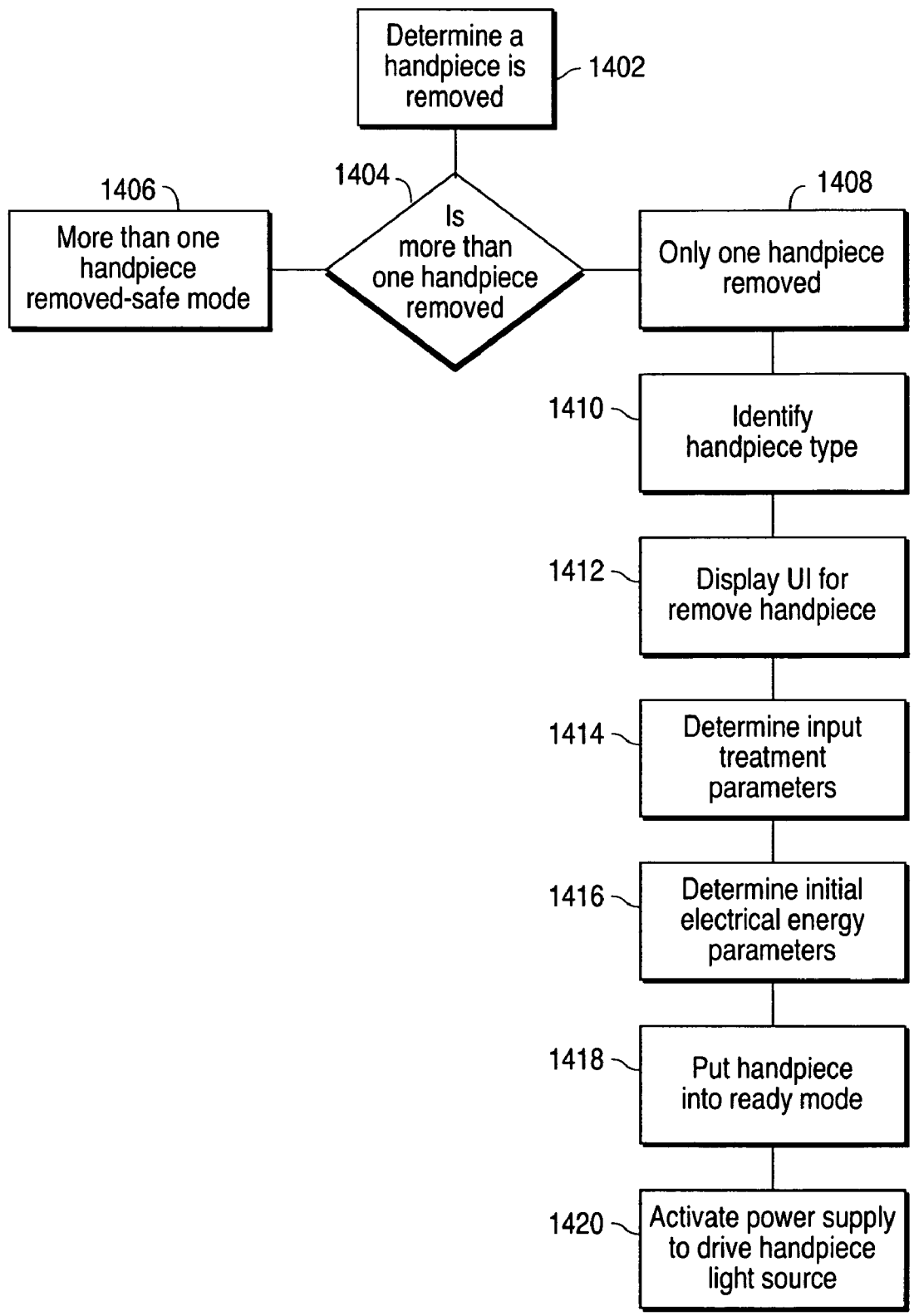
FIG. 14 shows a method of an embodiment herein.

FIG. 14 is a flow chart illustrating a method of an embodiment herein. At 1402 a determination is made that a hand piece is removed form the hand piece management unit. A determination 1404 is then made if more than one of the hand pieces is removed. If more than one hand piece is removed than the operation of the system is put into a safe mode 1406 so that none of the light sources can be activated. If a determination is made that only one hand piece has been removed 1408, then the operation toward activation of the light source of the removed hand piece can proceed. If only one hand piece is removed then the hand piece and its corresponding light source are identified 1410. The appropriate user interface for the removed hand piece and its light source is displayed 1412. Based on the user input to the user interface treatment parameters such as fluence, pulse duration, number of pulses, as maybe appropriate for the light source are determined 1114. Based on the treatment parameters, the electrical energy to be applied to the light source is determined 1416. In response to user input the light source for the hand piece is put into ready mode 1418. The controller for the power supply, or another processor for the system can be loaded with different algorithms and data for determining electrical output by the power supply. The controller of the power supply will then output electrical energy to drive the light source 1420 in response to a user input, such as stepping on a foot switch. Further the operation of the power supply can be modified based on signals received from different sensors such as current sensors, photodetectors and temperature detectors.

Figure 16:
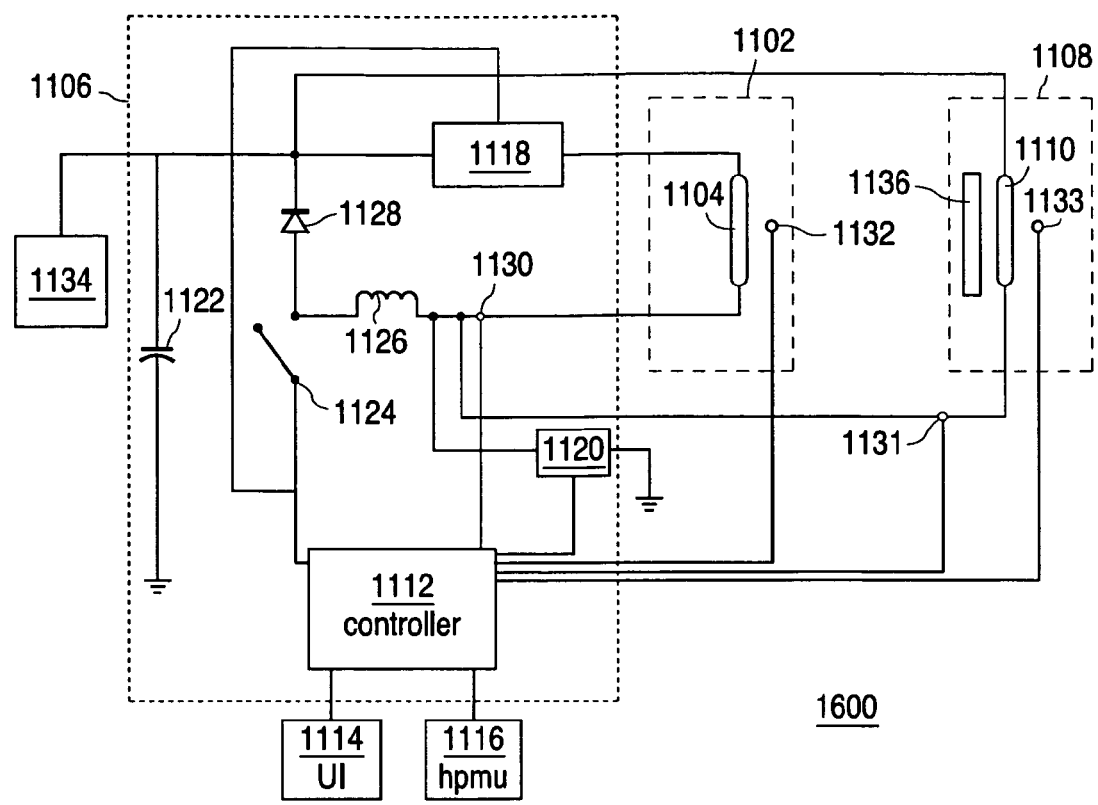
FIG. 16 shows an embodiment of a system herein.

FIG. 16 shows another embodiment of a system 1600. The system 1600 is very similar to the system discussed in connection with FIG. 11. The operation of most of the elements in the system 1600 is illustrated in connection with the discussion of the corresponding elements shown in the system 1100 of FIG. 11. However, FIG. 16 provides for one additional component which power relay or switch 1118 which is provided in series with the light source 1104 of the removable handpiece 1102. In one embodiment when the controller determines that the removable handpiece 1102 coupled to the power supply includes a flashlamp type of light source, then the switch 1118 will remain in a closed position, and the controller will user the simmer circuit to direct the current to either of the flashlamps 1102 or 1104, in the manner described above. If it is determined that the light source of the removable handpiece is another type of light source, such as a filament lamp, then the simmer may not provide an effective way to control the output of power from the power supply 1106. This is because when the filament light source is coupled to the high power output of the power supply the filament will represent a very low impedance across the output of the power supply, and the operation of the simmer circuit would not operate to raise or lower the impedance of the filament, as it does in the case of a flashlamp. Thus, system 1600 provides a switch 1118 which the controller 1112 can control. When the controller 1112 senses that the filament light source is coupled to the system, and that the user of the system desires to drive the filament light source, then the controller will close the switch 1118, and in response to a user input, apply power to the filament light source. Conversely, when the filament light source is connected to the system, but the controller determines that the user desires to drive the high power laser, the controller will open the switch 1118, and put the flashlamp 1102 in conductive mode using the simmer circuit 1120.

One of the advantages of using a controllable power supply is that the power supply can be programmed for a wide range of different light sources, and as new light sources and treatments are developed the controller of the power supply can be programmed, or otherwise controlled to output a wide range of different electrical pulses as may be most beneficial for a particular treatment using a particular light source.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

What is claimed is:

1. A light treatment apparatus comprising:
   a first handpiece for generating a first form of therapeutic radiation;
   a second handpiece for generating a second form of therapeutic radiation;
   a support for holding the first and second handpieces; and
   a circuit for monitoring when a handpiece has been removed from the support and for allowing the first handpiece to be actuated only if the first handpiece has been removed from the support and the second handpiece has not been removed from the support and for allowing the second handpiece to be actuated only if the second handpiece has been removed from the support and the first handpiece has not been removed from the support.

2. An apparatus as recited in claim 1, wherein said first handpiece includes a flashlamp.

3. An apparatus as recited in claim 2, further including a console containing a laser and wherein an optical fiber transmits light from the laser to the second handpiece.

4. An apparatus as recited in claim 1, wherein said first handpiece includes a filament lamp.

5. An apparatus as recited in claim 4, further including a console containing a laser and wherein an optical fiber transmits light from the laser to the second handpiece.

6. An apparatus as recited in claim 1, further including a display interface which permits the user to input treatment parameters and wherein the interface only displays parameters associated with a handpiece that can be actuated according to the monitoring circuit.

7. An apparatus as recited in claim 1, wherein said support includes sensors which are coupled to the monitoring circuit.

8. A method of operating a light treatment device having a detection circuit, and first and second handpieces for generating therapeutic radiation and wherein the handpieces are held in a support, said method comprising the steps of:
determining, via the detection circuit, whether the handpieces are located in the support or removed from the support; and
activating, via the detection circuit, one of the handpieces only if that handpiece has been removed from the support and the other handpiece has not been removed from the support.

9. A method as recited in claim 8, wherein said first handpiece includes a flashlamp.

10. A method as recited in claim 9, wherein the device includes a console containing a laser and wherein an optical fiber transmits light from the laser to the second handpiece.

11. A method as recited in claim 8, wherein said first handpiece includes a filament lamp.

12. A method as recited in claim 11, wherein the device includes a console containing a laser and wherein an optical fiber transmits light from the laser to the second handpiece.

13. A method as recited in claim 8, further including the step of displaying input treatment parameters associated with the handpiece that can be actuated.

14. A method as recited in claim 8, wherein said support includes sensors and wherein said sensors are monitored during said determining step.

* * * * *